United States Patent [19]
Knowles et al.

[11] Patent Number: 5,766,915
[45] Date of Patent: *Jun. 16, 1998

[54] YEAST STRAINS PRODUCING CELLULOLYTIC ENZYMES AND METHODS AND MEANS FOR CONSTRUCTING THEM

[75] Inventors: Jonathan Knowles, Suisse, Switzerland; Merja Penttilä, Helsinki, Finland; Tuula Teeri; Helena Nevalainen, both of Espoo, Finland; Paivi Lehtovaara-Helenius; Sirpa Aho, both of Helsinki, Finland; Sunee Nitisinprasert, Bangkok, Thailand; Marja Paloheimo; Sirkka Keränen, both of Helsinki, Finland

[73] Assignee: Alko-Yhtiot Oy (Alko Group Ltd.), Helsinki, Finland

[*] Notice: The term of this patent shall not extend beyond the expiration date of Pat. No. 5,343,670.

[21] Appl. No.: 380,438

[22] Filed: Jan. 30, 1995

Related U.S. Application Data

[63] Continuation of Ser. No. 801,161, Nov. 29, 1991, abandoned, which is a continuation-in-part of Ser. No. 418,154, Oct. 6, 1989, abandoned, which is a division of Ser. No. 817,942, PCT/FI85/00039 filed on Apr. 12, 1985, Pat. No. 4,894,338.

[30] Foreign Application Priority Data

Apr. 13, 1984 [FI] Finland ................... 841500

[51] Int. Cl.$^6$ ................ C12N 9/42; C12N 1/19; C12N 15/81; C12N 15/56
[52] U.S. Cl. ................ 435/209; 435/254.21; 435/320.1; 435/172.3; 536/23.2; 536/24.32
[58] Field of Search .................. 435/252.53, 69.8, 435/172.3, 209, 254.11, 254.2, 254.21, 945; 536/23.2, 23.74

[56] References Cited

U.S. PATENT DOCUMENTS

| | | | |
|---|---|---|---|
| 4,338,397 | 7/1982 | Gilbert et al. | 435/69.1 |
| 4,794,175 | 12/1988 | Nunberg et al. | 536/24.3 |

OTHER PUBLICATIONS

James et al., Third Bioenergy R&D Seminar, pp. 135–139 (1981).
Enari, "Microbiol. Cellulases," in Microbiol. Enzymes and Biotechnol., Wm. M. Fogart, ed., Appl. Science, Pub., London, pp. 183–223.
Stahlberg et al., Eur. J. Biochem., 173:179–183 (1988).
Uhlmann, Chemical Reviews, vol. 90(4) p. 576 (1990).
Lichtenstein, Nature, 333: 801–802 (1988).
Penttilä, M.E. et al., Gene 5:253–263 (1986).
Montenecourt, B.S., Trends in Biotechnology 1:156–161(1983).
Shoemaker, S. et al., Biotechnology:687–690 (1983).
Van Arsdell, J.N. et al., Bio/Technology 5:60–64 (1987).
Penttilä, M.E. et al., Yeast 3:175–185 (1987).
Gritzali, M. et al., Chem. Abstr. 93, #21423a (1980) (The dissertation itself is document AT9).
Churilova, I.V. et al., Chem. Abstr. 93, #21382m (1980).
Seligy, V.L. et al., Gene Expression in Yeast, Proceedings of the Alko Yeast Symposium, Helsinki, (Korhola et al. ed.) pp. 167–185 (1983).
Whittle, D.J. et al., Gene 17:139–145 (1982).
Nitisinprasert, S., Dissertation Dept. Microbiol., Univ. of Helsinki, Finland (1990).
Knowles, J. et al., Trends in Biotechnology 5:255–261 (1987).
Aho, S., FEBS Letters 291(1):45–49 (1991).
James, A.P. et al., Chem. Abstr. 97, #4552g (1981).
Aho, S., et al., Eur. J. Biochem. 200:643–649 (1991).
Arffman, A. et al., Yeast 6:S438 (1990).
Mitsuishi, Y. et al., FEBS Letters 275:135–138 (1990).
Ong, E. et al., TIBTECH 7:239–243 (1989).
Tomme, P. et al., FEBS Letters 243(2):239–243 (1989).
Warren, R.A.J. et al., Gene 61:421–427 (1987).
Warren, R.A.J. et al., Proteins 1:335–341 (1986).
Aho, S. et al., Biochim. Biophys. Acta 1087:137–141 (1990) 23 Oct. 1990.
Gilkes, N.R. et al., J. Biol. Chem. 263(21):10401–10407 (1988).
Niku–Paavola, M.-L. et al., Biochem. J. 231:75–81 (1985).
Claeyssens, M. et al., In: Trichoderma Cellulases, pp. 1–11, Kubicek et al. ed., (1990).
Gritzali, M., Dissertation, Dept. of Biochemistry and Nutrition, Virginia Polytechnic Inst. and State Univ. (1979).
Aho, S. et al., "Characterization Of Monoclonal Antibodies Against Trichoderma reesi Cellulases," Fourth Nordic Symposium on Gene Technology in Basic and Applied Research, Feb. 10–14, 1990, Storlien, Sweden, Abstract, p. 29.

Primary Examiner—Nancy T. Vogel
Attorney, Agent, or Firm—Sterne, Kessler, Goldstein & Fox P.L.L.C.

[57] ABSTRACT

Functional derivatives of endoglucanase I (EGI), and the cloning and recombinant expression thereof, are described.

7 Claims, 11 Drawing Sheets

```
                                        1
                                        Met Ala Pro Ser Val Thr Leu Pro Leu Thr Ala Ile Leu Ala Ile Ala Arg Leu Val Ala Ala Gln Pro Gly Thr
                                        TTGTCCCAAA ATG GCG CCC TCA GTT ACA CTG CCG TTG ACC ACG GCC ATC CTG GCC ATT GCC CGG CTC GTC GCC GCC CAG CAA CCG GGT ACC    91
                                                                                                                                       Kpn I
        30                                                                      40                                               50
Ser Thr Pro Glu Val His Pro Lys Leu Thr Thr Tyr Lys Cys Thr Lys Ser Gly Gly Cys Val Ala Gln Asp Thr Ser Val Val Leu Asp
AGC ACC CCC GAG GTC CAT CCC AAG TTG ACA ACC TAC AAG TGT ACA AAG TCC GGG GGC TGC GTG GCC CAG GAC ACC TCG GTC GTC CTT GAC    161

60                                                                      70                                      *        80
Trp Asn Tyr Arg Trp Met His Asp Ala Asn Tyr Asn Ser Cys Thr Val Asn Gly Gly Val Asn Thr Thr Leu Cys Pro Asp Glu Ala Thr
TGG AAC TAC CGC TGG ATG CAC GAC GCA AAC TAC AAC TCG TGC ACC GTC AAC GGC GGC GTC AAC ACC ACC CTC TGC CCT GAC GAG GCG ACC    271

90                                                                      100                                              110
Cys Gly Lys Asn Cys Phe Ile Glu Gly Val Asp Tyr Ala Ala Ser Gly Val Thr Thr Ser Gly Ser Ser Leu Thr Met Asn Gln Tyr Met
TGT GGC AAG AAC TGC TTC ATC GAG GGC GTC GAC TAC GCC GCC TCG GGC GTC ACG ACC TCG GGC AGC AGC CTC ACC ATG AAC CAG TAC ATG    361
                                                    Sal I 120                                                                     130                                              140
Pro Ser Ser Gly Gly Tyr Ser Ser Val Ser Pro Arg Leu Tyr Leu Leu Asp Ser Asp Gly Glu Tyr Val Met Leu Lys Leu Asn Gly
CCC AGC AGC GGC TCT GGC TAC AGC AGC GTC TCT CCT CGG CTG TAT CTC CTG GAC TCT GAC GGT GAG TAC GTG ATG CTG AAG CTG AAC GGC    451

150                                                                     160               *                              170
Gln Glu Leu Ser Phe Asp Val Asp Leu Ser Ala Leu Pro Cys Gly Glu Asn Gly Ser Leu Tyr Leu Ser Gln Met Asp Glu Asn Gly Gly
CAG GAG CTG AGC TTC GAC GTC GAC CTC TCT GCT CTG CCC TGT GGA GAG AAC GGC TCG CTC TAC CTG TCT CAG ATG GAC GAG AAC GGG GGC    541
                        Sal I
```

FIG.2A

```
180                    190                     200
Ala Asn Gln Tyr Asn Thr Ala Gly Ala Asn Tyr Gly Tyr Ser Gly Tyr Cys Asp Ala Gln Cys Pro Val Gln Thr Trp Arg Asn Gly Thr Leu    631
GCC AAC CAG TAT AAC ACG GCC GGT GCC AAC TAC GGG AGC TAC TGC GAT GCT CAG TGC CCC GTC CAG ACA TGG AGG AAC GGC ACC CTC 210                    220                     230
Asn Thr Ser His Gln Gly Phe Cys Cys Asn Glu Met Asp Ile Leu Glu Gly Asn Ser Arg Ala Asn Ala Leu Thr Pro His Ser Cys Thr       721
AAC ACT AGC CAC CAG GGC TTC TGC TGC AAC GAG ATG GAT ATC CTG GAG GGC AAC TCG AGG GCC AAT GCC TTG ACC CCT CAC TCT TGC ACG
                                                                                    Xho I 240                    250                     260
Ala Thr Ala Cys Asp Ser Ala Gly Cys Gly Phe Asn Pro Tyr Gly Ser Gly Tyr Lys Se    r Tyr Tyr Gly Pro Gly                       816
GCC ACG GCC TGC GAC TCT GCC GGT TGC GGC TTC AAC CCC TAT GGC AGC GGC TAC AAA AG  gtgagcctgat gccactacta cccctttcct ggcgc C TAC TAC GGC CCC GGA 270
                                         Asp Thr Val Asp Thr Ser Lys Thr Phe Thr Ile Ile Thr Gln Phe                        911
                                         GAT ACC GTT GAC ACC TCC AAG ACC TTC ACC ATC ATC ACC CAG TTC 280                    290                     300
Asn Thr Asp Asn Gly Ser Pro Ser Gly Asn Leu Val Ser Ile Thr Arg Lys Tyr Gln Gln Asn Gly Val Asp Ile Pro Ser Ala Gln Pro       1001
AAC ACG GAC AAC GGC TCG CCC TCG GGC AAC CTT GTG AGC ATC ACC AGG AAG TAC CAG CAA AAC GGC GTC GAC ATC CCC AGC GCC CAG CCC
                                                                                                    Sal I 310                    320                     330
Gly Gly Asp Thr Ile Ser Ser Cys Pro Ser Ala Ser Ala Tyr Gly Gly Leu Ala Thr Met Gly Lys Ala Leu Ser Ser Gly Met Val Leu      1091
GGC GGC GAC ACC ATC TCG TCC TGC CCG TCC GCC TCA GCC TAC GGC GGC CTC GCC ACC ATG GGC AAG GCC CTG AGC AGC GGC ATG GTG CTC
```

FIG.2B

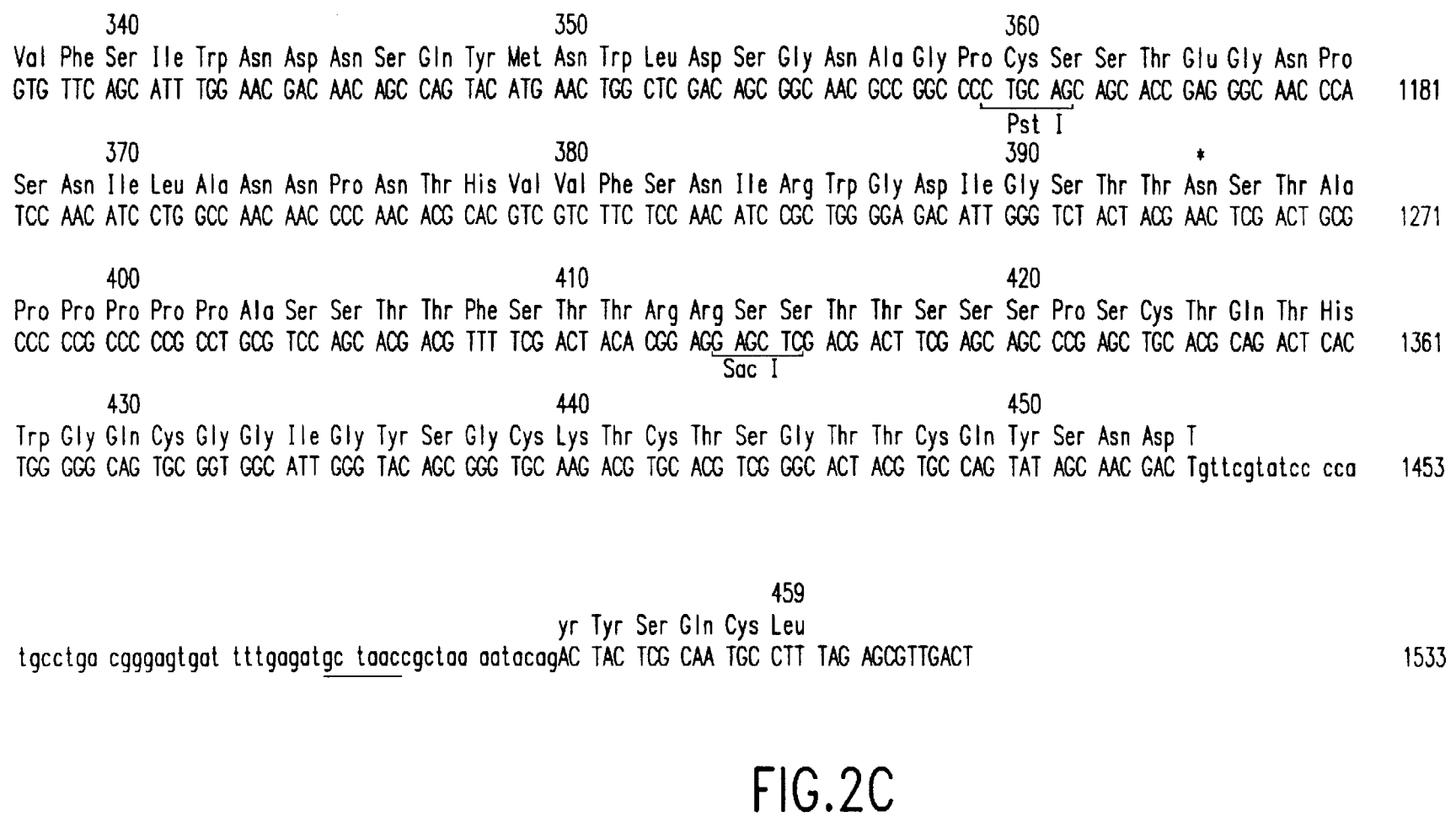

```
                340                                        350                                            360
Val Phe Ser Ile Trp Asn Asp Asn Ser Gln Tyr Met Asn Trp Leu Asp Ser Gly Asn Ala Gly Pro Cys Ser Ser Thr Glu Gly Asn Pro
GTG TTC AGC ATT TGG AAC GAC AAC AGC CAG TAC ATG AAC TGG CTC GAC AGC GGC AAC GCC GGC CCC TGC AGC AGC ACC GAG GGC AAC CCA   1181
                                                                                                  ─────
                                                                                                  Pst I
                370                                        380                                            390        *
Ser Asn Ile Leu Ala Asn Asn Pro Asn Thr His Val Phe Ser Asn Ile Arg Trp Gly Asp Ile Gly Ser Thr Thr Asn Ser Thr Ala
TCC AAC ATC CTG GCC AAC AAC CCC AAC ACT CAC GTC TTC TCC AAC ATC CGC TGG GGA GAC ATT GGG TCT ACT ACG AAC TCG ACT GCG       1271

400                                        410                                            420
Pro Pro Pro Pro Ala Ser Thr Ser Ser Thr Phe Ser Thr Thr Arg Arg Ser Ser Thr Thr Ser Ser Pro Ser Cys Thr Gln Thr His
CCC CCG CCG CCC CCG GCG TCC CCT TCG AGC ACG ACG TTT TCC ACT ACA CGG AGG AGC TCC ACG ACT TCG AGC CCG AGC TGC ACG CAG ACT CAC  1361
                                                                  ─────
                                                                  Sac I
                430                                        440                                            450
Trp Gly Gln Cys Gly Gly Ile Gly Tyr Ser Gly Cys Lys Thr Cys Thr Ser Gly Thr Thr Cys Gln Tyr Ser Asn Asp Ser T
TGG GGG CAG TGC GGT GGT ATT GGG TAC AGC GGG TGC AAG ACG TGC ACG TCG GGC ACT ACG TGC CAG TAT AGC AAC GAC Tgttcgtatcc cca     1453

459
                                                    yr Tyr Ser Gln Cys Leu
tgcctga cgggagtgat tttgagatgc taaccgctaa aatacagAC TAC TCG CAA TGC CTT TAG AGCCGTTGACT                                    1533
```

FIG.2C

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 1527 base pairs
      ( B ) TYPE: nucleic acid
      ( C ) STRANDEDNESS: both
      ( D ) TOPOLOGY: linear ( i i ) MOLECULE TYPE: DNA ( i x ) FEATURE:
      ( A ) NAME/KEY: exon
      ( B ) LOCATION: 11..780

( i x ) FEATURE:
      ( A ) NAME/KEY: intron
      ( B ) LOCATION: 781..850

( i x ) FEATURE:
      ( A ) NAME/KEY: exon
      ( B ) LOCATION: 851..1440

( i x ) FEATURE:

( A ) NAME/KEY: intron
( B ) LOCATION: 1441..1497

( i x ) FEATURE:
( A ) NAME/KEY: CDS
( B ) LOCATION: join(11..780, 851..1440, 1498..1514)

( i x ) FEATURE:
( A ) NAME/KEY: exon
( B ) LOCATION: 1498..1514

( x i ) SEQUENCE DESCRIPTION: SEQ ID NO:1:

| | | | | | | | | | | | | | | | |
|---|---|---|---|---|---|---|---|---|---|---|---|---|---|---|---|
| TTGTCCCAAA | ATG | GCG | CCC | TCA | GTT | ACA | CTG | CCG | TTG | ACC | ACG | GCC | ATC | | 49 |
| | Met | Ala | Pro | Ser | Val | Thr | Leu | Pro | Leu | Thr | Thr | Ala | Ile | | |
| | 1 | | | | 5 | | | | | 10 | | | | | |
| CTG | GCC | ATT | GCC | CGG | CTC | GTC | GCC | GCC | CAG | CAA | CCG | GGT | ACC | AGC ACC | 97 |
| Leu | Ala | Ile | Ala | Arg | Leu | Val | Ala | Ala | Gln | Gln | Pro | Gly | Thr | Ser Thr | |
| 15 | | | | | 20 | | | | | 25 | | | | | |
| CCC | GAG | GTC | CAT | CCC | AAG | TTG | ACA | ACC | TAC | AAG | TGT | ACA | AAG | TCC GGG | 145 |
| Pro | Glu | Val | His | Pro | Lys | Leu | Thr | Thr | Tyr | Lys | Cys | Thr | Lys | Ser Gly | |
| 30 | | | | | 35 | | | | | 40 | | | | 45 | |
| GGG | TGC | GTG | GCC | CAG | GAC | ACC | TCG | GTG | GTC | CTT | GAC | TGG | AAC | TAC CGC | 193 |
| Gly | Cys | Val | Ala | Gln | Asp | Thr | Ser | Val | Val | Leu | Asp | Trp | Asn | Tyr Arg | |
| | | | | 50 | | | | | 55 | | | | | 60 | |
| TGG | ATG | CAC | GAC | GCA | AAC | TAC | AAC | TCG | TGC | ACC | GTC | AAC | GGC | GGC GTC | 241 |
| Trp | Met | His | Asp | Ala | Asn | Tyr | Asn | Ser | Cys | Thr | Val | Asn | Gly | Gly Val | |
| | | | 65 | | | | | 70 | | | | | 75 | | |
| AAC | ACC | ACG | CTC | TGC | CCT | GAC | GAG | GCG | ACC | TGT | GGC | AAG | AAC | TGC TTC | 289 |
| Asn | Thr | Thr | Leu | Cys | Pro | Asp | Glu | Ala | Thr | Cys | Gly | Lys | Asn | Cys Phe | |
| | | 80 | | | | | 85 | | | | | 90 | | | |
| ATC | GAG | GGC | GTC | GAC | TAC | GCC | GCC | TCG | GGC | GTC | ACG | ACC | TCG | GGC AGC | 337 |
| Ile | Glu | Gly | Val | Asp | Tyr | Ala | Ala | Ser | Gly | Val | Thr | Thr | Ser | Gly Ser | |
| | 95 | | | | | 100 | | | | | 105 | | | | |
| AGC | CTC | ACC | ATG | AAC | CAG | TAC | ATG | CCC | AGC | AGC | TCT | GGC | GGC | TAC AGC | 385 |
| Ser | Leu | Thr | Met | Asn | Gln | Tyr | Met | Pro | Ser | Ser | Ser | Gly | Gly | Tyr Ser | |
| 110 | | | | | 115 | | | | | 120 | | | | 125 | |
| AGC | GTC | TCT | CCT | CGG | CTG | TAT | CTC | CTG | GAC | TCT | GAC | GGT | GAG | TAC GTG | 433 |
| Ser | Val | Ser | Pro | Arg | Leu | Tyr | Leu | Leu | Asp | Ser | Asp | Gly | Glu | Tyr Val | |
| | | | 130 | | | | | 135 | | | | | 140 | | |
| ATG | CTG | AAG | CTC | AAC | GGC | CAG | GAG | CTG | AGC | TTC | GAC | GTC | GAC | CTC TCT | 481 |
| Met | Leu | Lys | Leu | Asn | Gly | Gln | Glu | Leu | Ser | Phe | Asp | Val | Asp | Leu Ser | |
| | | | 145 | | | | | 150 | | | | | 155 | | |
| GCT | CTG | CCG | TGT | GGA | GAG | AAC | GGC | TCG | CTC | TAC | CTG | TCT | CAG | ATG GAC | 529 |
| Ala | Leu | Pro | Cys | Gly | Glu | Asn | Gly | Ser | Leu | Tyr | Leu | Ser | Gln | Met Asp | |
| | | 160 | | | | | 165 | | | | | 170 | | | |
| GAG | AAC | GGG | GGC | GCC | AAC | CAG | TAT | AAC | ACG | GCC | GGT | GCC | AAC | TAC GGG | 577 |
| Glu | Asn | Gly | Gly | Ala | Asn | Gln | Tyr | Asn | Thr | Ala | Gly | Ala | Asn | Tyr Gly | |
| | 175 | | | | | 180 | | | | | 185 | | | | |
| AGC | GGC | TAC | TGC | GAT | GCT | CAG | TGC | CCC | GTC | CAG | ACA | TGG | AGG | AAC GGC | 625 |
| Ser | Gly | Tyr | Cys | Asp | Ala | Gln | Cys | Pro | Val | Gln | Thr | Trp | Arg | Asn Gly | |
| 190 | | | | | 195 | | | | | 200 | | | | 205 | |
| ACC | CTC | AAC | ACT | AGC | CAC | CAG | GGC | TTC | TGC | TGC | AAC | GAG | ATG | GAT ATC | 673 |
| Thr | Leu | Asn | Thr | Ser | His | Gln | Gly | Phe | Cys | Cys | Asn | Glu | Met | Asp Ile | |
| | | | | 210 | | | | | 215 | | | | | 220 | |
| CTG | GAG | GGC | AAC | TCG | AGG | GCG | AAT | GCC | TTG | ACC | CCT | CAC | TCT | TGC ACG | 721 |
| Leu | Glu | Gly | Asn | Ser | Arg | Ala | Asn | Ala | Leu | Thr | Pro | His | Ser | Cys Thr | |
| | | | 225 | | | | | 230 | | | | | 235 | | |
| GCC | ACG | GCC | TGC | GAC | TCT | GCC | GGT | TGC | GGC | TTC | AAC | CCC | TAT | GGC AGC | 769 |
| Ala | Thr | Ala | Cys | Asp | Ser | Ala | Gly | Cys | Gly | Phe | Asn | Pro | Tyr | Gly Ser | |
| | | 240 | | | | | 245 | | | | | 250 | | | |
| GGC | TAC | AAA | AG | GTGAGCCTGA | TGCCACTACT | ACCCCTTTCC | TGGCGCTCTC | | | | | | | | 820 |
| Gly | Tyr | Lys | Ser | | | | | | | | | | | | |
| | | 255 | | | | | | | | | | | | | |

-continued

| | | | | | | | |
|---|---|---|---|---|---|---|---|
| GCGGTTTTCC ATGCTGACAT GGTTTTCCAG C TAC TAC GGC CCC GGA GAT ACC | | | | | | | 872 |
| | | | Tyr Tyr Gly Pro Gly Asp Thr | | | | |
| | | | 260 | | | | |

```
GTT GAC ACC TCC AAG ACC TTC ACC ATC ATC ACC CAG TTC AAC ACG GAC      920
Val Asp Thr Ser Lys Thr Phe Thr Ile Ile Thr Gln Phe Asn Thr Asp
265             270             275             280

AAC GGC TCG CCC TCG GGC AAC CTT GTG AGC ATC ACC CGC AAG TAC CAG      968
Asn Gly Ser Pro Ser Gly Asn Leu Val Ser Ile Thr Arg Lys Tyr Gln
                285             290             295

CAA AAC GGC GTC GAC ATC CCC AGC GCC CAG CCC GGC GGC GAC ACC ATC     1016
Gln Asn Gly Val Asp Ile Pro Ser Ala Gln Pro Gly Gly Asp Thr Ile
            300             305             310

TCG TCC TGC CCG TCC GCC TCA GCC TAC GGC GGC CTC GCC ACC ATG GGC     1064
Ser Ser Cys Pro Ser Ala Ser Ala Tyr Gly Gly Leu Ala Thr Met Gly
        315             320             325

AAG GCC CTG AGC AGC GGC ATG GTG CTC GTG TTC AGC ATT TGG AAC GAC     1112
Lys Ala Leu Ser Ser Gly Met Val Leu Val Phe Ser Ile Trp Asn Asp
330             335             340

AAC AGC CAG TAC ATG AAC TGG CTC GAC AGC GGC AAC GCC GGC CCC TGC     1160
Asn Ser Gln Tyr Met Asn Trp Leu Asp Ser Gly Asn Ala Gly Pro Cys
345             350             355             360

AGC AGC ACC GAG GGC AAC CCA TCC AAC ATC CTG GCC AAC AAC CCC AAC     1208
Ser Ser Thr Glu Gly Asn Pro Ser Asn Ile Leu Ala Asn Asn Pro Asn
                365                 370             375

ACG CAC GTC GTC TTC TCC AAC ATC CGC TGG GGA GAC ATT GGG TCT ACT     1256
Thr His Val Val Phe Ser Asn Ile Arg Trp Gly Asp Ile Gly Ser Thr
            380             385             390

ACG AAC TCG ACT GCG CCC CCG CCC CCG CCT GCG TCC AGC ACG ACG TTT     1304
Thr Asn Ser Thr Ala Pro Pro Pro Pro Pro Ala Ser Ser Thr Thr Phe
        395             400             405

TCG ACT ACA CGG AGG AGC TCG ACG ACT TCG AGC AGC CCG AGC TGC ACG     1352
Ser Thr Thr Arg Arg Ser Ser Thr Thr Ser Ser Ser Pro Ser Cys Thr
410             415             420

CAG ACT CAC TGG GGG CAG TGC GGT GGC ATT GGG TAC AGC GGG TGC AAG     1400
Gln Thr His Trp Gly Gln Cys Gly Gly Ile Gly Tyr Ser Gly Cys Lys
425             430             435             440

ACG TGC ACG TCG GGC ACT ACG TGC CAG TAT AGC AAC GAC   T GTTCGTATCC  1450
Thr Cys Thr Ser Gly Thr Thr Cys Gln Tyr Ser Asn Asp
                445             450
```

| | | | |
|---|---|---|---|
| CCATGCCTGA CGGGAGTGAT TTTGAGATGC TAACCGCTAA AATACAG AC TAC TCG | | | 1505 |
| | | Tyr Tyr Ser | |
| | | 455 | |

```
CAA TGC CTT TAGAGCGTTG ACT                                          1527
Gln Cys Leu
```

( 2 ) INFORMATION FOR SEQ ID NO:2:

( i ) SEQUENCE CHARACTERISTICS:
        ( A ) LENGTH: 459 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20              25              30

His Pro Lys Leu Thr Thr Tyr Lys Cys Thr Lys Ser Gly Gly Cys Val
        35                  40              45
```

-continued

| | | | | | | | | | | | | | | |
|---|---|---|---|---|---|---|---|---|---|---|---|---|---|---|
| Ala | Gln | Asp | Thr | Ser | Val | Val | Leu | Asp | Trp | Asn | Tyr | Arg | Trp | Met | His |
| | 50 | | | | | 55 | | | | | 60 | | | | |
| Asp | Ala | Asn | Tyr | Asn | Ser | Cys | Thr | Val | Asn | Gly | Gly | Val | Asn | Thr | Thr |
| 65 | | | | | 70 | | | | | 75 | | | | | 80 |
| Leu | Cys | Pro | Asp | Glu | Ala | Thr | Cys | Gly | Lys | Asn | Cys | Phe | Ile | Glu | Gly |
| | | | | 85 | | | | | 90 | | | | | 95 | |
| Val | Asp | Tyr | Ala | Ala | Ser | Gly | Val | Thr | Ser | Gly | Ser | Ser | Leu | Thr |
| | | | 100 | | | | | 105 | | | | 110 | | |
| Met | Asn | Gln | Tyr | Met | Pro | Ser | Ser | Gly | Gly | Tyr | Ser | Ser | Val | Ser |
| | | 115 | | | | | 120 | | | | | 125 | | | |
| Pro | Arg | Leu | Tyr | Leu | Leu | Asp | Ser | Asp | Gly | Glu | Tyr | Val | Met | Leu | Lys |
| | 130 | | | | | 135 | | | | | 140 | | | | |
| Leu | Asn | Gly | Gln | Glu | Leu | Ser | Phe | Asp | Val | Asp | Leu | Ser | Ala | Leu | Pro |
| 145 | | | | | 150 | | | | | 155 | | | | | 160 |
| Cys | Gly | Glu | Asn | Gly | Ser | Leu | Tyr | Leu | Ser | Gln | Met | Asp | Glu | Asn | Gly |
| | | | | 165 | | | | | 170 | | | | | 175 | |
| Gly | Ala | Asn | Gln | Tyr | Asn | Thr | Ala | Gly | Ala | Asn | Tyr | Gly | Ser | Gly | Tyr |
| | | | 180 | | | | | 185 | | | | | 190 | | |
| Cys | Asp | Ala | Gln | Cys | Pro | Val | Gln | Thr | Trp | Arg | Asn | Gly | Thr | Leu | Asn |
| | | | 195 | | | | 200 | | | | | 205 | | | |
| Thr | Ser | His | Gln | Gly | Phe | Cys | Cys | Asn | Glu | Met | Asp | Ile | Leu | Glu | Gly |
| | 210 | | | | | 215 | | | | | 220 | | | | |
| Asn | Ser | Arg | Ala | Asn | Ala | Leu | Thr | Pro | His | Ser | Cys | Thr | Ala | Thr | Ala |
| 225 | | | | | 230 | | | | | 235 | | | | | 240 |
| Cys | Asp | Ser | Ala | Gly | Cys | Gly | Phe | Asn | Pro | Tyr | Gly | Ser | Gly | Tyr | Lys |
| | | | | 245 | | | | | 250 | | | | | 255 | |
| Ser | Tyr | Tyr | Gly | Pro | Gly | Asp | Thr | Val | Asp | Thr | Ser | Lys | Thr | Phe | Thr |
| | | | 260 | | | | | 265 | | | | | 270 | | |
| Ile | Ile | Thr | Gln | Phe | Asn | Thr | Asp | Asn | Gly | Ser | Pro | Ser | Gly | Asn | Leu |
| | | 275 | | | | | 280 | | | | | 285 | | | |
| Val | Ser | Ile | Thr | Arg | Lys | Tyr | Gln | Gln | Asn | Gly | Val | Asp | Ile | Pro | Ser |
| | 290 | | | | | 295 | | | | | 300 | | | | |
| Ala | Gln | Pro | Gly | Gly | Asp | Thr | Ile | Ser | Ser | Cys | Pro | Ser | Ala | Ser | Ala |
| 305 | | | | | 310 | | | | | 315 | | | | | 320 |
| Tyr | Gly | Gly | Leu | Ala | Thr | Met | Gly | Lys | Ala | Leu | Ser | Ser | Gly | Met | Val |
| | | | | 325 | | | | | 330 | | | | | 335 | |
| Leu | Val | Phe | Ser | Ile | Trp | Asn | Asp | Asn | Ser | Gln | Tyr | Met | Asn | Trp | Leu |
| | | | 340 | | | | | 345 | | | | | 350 | | |
| Asp | Ser | Gly | Asn | Ala | Gly | Pro | Cys | Ser | Ser | Thr | Glu | Gly | Asn | Pro | Ser |
| | | 355 | | | | | 360 | | | | | 365 | | | |
| Asn | Ile | Leu | Ala | Asn | Asn | Pro | Asn | Thr | His | Val | Val | Phe | Ser | Asn | Ile |
| | 370 | | | | | 375 | | | | | 380 | | | | |
| Arg | Trp | Gly | Asp | Ile | Gly | Ser | Thr | Thr | Asn | Ser | Thr | Ala | Pro | Pro | Pro |
| 385 | | | | | 390 | | | | | 395 | | | | | 400 |
| Pro | Pro | Ala | Ser | Ser | Thr | Thr | Phe | Ser | Thr | Arg | Arg | Ser | Ser | Thr |
| | | | | 405 | | | | | 410 | | | | | 415 | |
| Thr | Ser | Ser | Ser | Pro | Ser | Cys | Thr | Gln | Thr | His | Trp | Gly | Gln | Cys | Gly |
| | | | 420 | | | | | 425 | | | | | 430 | | |
| Gly | Ile | Gly | Tyr | Ser | Gly | Cys | Lys | Thr | Cys | Thr | Ser | Gly | Thr | Thr | Cys |
| | | | 435 | | | | | 440 | | | | | 445 | | |
| Gln | Tyr | Ser | Asn | Asp | Tyr | Tyr | Ser | Gln | Cys | Leu |
| | 450 | | | | | 455 | | | | |

( 2 ) INFORMATION FOR SEQ ID NO:3:

( i ) SEQUENCE CHARACTERISTICS:
    ( A ) LENGTH: 22 amino acids
    ( B ) TYPE: amino acid
    ( C ) STRANDEDNESS: both
    ( D ) TOPOLOGY: linear ( i i ) MOLECULE TYPE: peptide ( x i ) SEQUENCE DESCRIPTION: SEQ ID NO:3:

```
Met Ala Pro Ser Val Thr Leu Pro Leu Thr Thr Ala Ile Leu Ala Ile
 1               5                  10                  15
    Ala Arg Leu Val Ala Ala
                 20
```

( 2 ) INFORMATION FOR SEQ ID NO:4:

( i ) SEQUENCE CHARACTERISTICS:
    ( A ) LENGTH: 24 base pairs
    ( B ) TYPE: nucleic acid
    ( C ) STRANDEDNESS: both
    ( D ) TOPOLOGY: linear ( i i ) MOLECULE TYPE: DNA ( x i ) SEQUENCE DESCRIPTION: SEQ ID NO:4:

ATATAAAACC AAAAGATCTC CCAT                   24

( 2 ) INFORMATION FOR SEQ ID NO:5:

( i ) SEQUENCE CHARACTERISTICS:
    ( A ) LENGTH: 52 base pairs
    ( B ) TYPE: nucleic acid
    ( C ) STRANDEDNESS: both
    ( D ) TOPOLOGY: linear ( i i ) MOLECULE TYPE: DNA ( x i ) SEQUENCE DESCRIPTION: SEQ ID NO:5:

CCAAAAGATC ATTCCCCCCC CCTATCTTAG TCCTTCTTGT TGTCCCAAAA TG    52

( 2 ) INFORMATION FOR SEQ ID NO:6:

( i ) SEQUENCE CHARACTERISTICS:
    ( A ) LENGTH: 48 base pairs
    ( B ) TYPE: nucleic acid
    ( C ) STRANDEDNESS: both
    ( D ) TOPOLOGY: linear ( i i ) MOLECULE TYPE: DNA ( x i ) SEQUENCE DESCRIPTION: SEQ ID NO:6:

TCAAGCAAAA AAAAAAAAA AAAAAAAAA AGGGGATCAG TCTCCCAT      48

YEAST STRAINS PRODUCING CELLULOLYTIC ENZYMES AND METHODS AND MEANS FOR CONSTRUCTING THEM

CROSS-REFERENCE TO RELATED APPLICATIONS

This application is a continuation of application Ser. No. 07/801,161, filed Nov. 29, 1991, abandoned, which is a continuation-in-part of application Ser. No. 07/418,154, abandoned filed Oct. 6, 1989, abandoned, which is a divisional of application Ser. No. 06/817,942, U.S. Pat. No. 4,944,338, filed Jan. 30, 1986, which is the national phase filing of application Ser. No. PCT/FI85/00039, filed on Apr. 12, 1985 in PCT.

FIELD OF THE INVENTION

This invention is in the field of molecular biology. Specifically, the invention is directed to shortened forms of endoglucanase I (EGI) produced by recombinant DNA methods, vectors encoding such shortened EGI, and recombinant hosts transformed therewith.

BACKGROUND OF THE INVENTION

Two cellobiohydrolases (CBH) and two or more endoglucanases (EG) of *Trichoderma reesei* (*T. reesei*) act synergistically to bring about efficient hydrolysis of native cellulose. The active sites of no cellulases have so far been characterized in detail but chemical modification of carboxyl groups of *T. reesei* cellobiohydrolase I (CBHI) and endoglucanase I (EGI) suggests that the glutamic acid, E126 in CBHI and the corresponding glutamic acid, E127 in EGI are essential for catalysis (P. Tomme and M. Claeyssens, *FEBS Lett.* 243:239–243 (1989); M. Claeyssens and P. Tomme, "*Trichoderma cellulases*" *Biochemistry, Genetics, Physiology and Application* (Kubicek et al., ed.), Technical Communications & Springer GmbH, pp. 1–11, (1990)). However, amino acids essential for catalytic activity are still undefined.

EGI is the same enzyme that has also been known and abbreviated in the art, especially the European art, as ENDO II. (The enzyme formerly known in the art as ENDO III is now abbreviated EGII.) Fungal and bacterial cellulases are composed of a core domain and a tail domain that contains a Thr-Ser or Thr-Pro-rich B-region and a conserved A-region (Knowles et al., *Trends Biotechnol.* 5:255–261 (1987); Warren et al., *Proteins* 1:335–341 (1986)). A distinct function has been suggested for each of these domains. The B-region is suggested to function as a flexible hinge between the two functional domains. The isolated core domain is able to degrade soluble cellulose (Ståhlberg et al, *Eur. J. Biochem.* 173:179–183 (1988)). Isolated tails have affinity for cellulose and are suggested to bind the enzyme to its substrate (Ong et al, *Trends Biotechnol.* 7:239–243 (1989)).

Genes for the two cellobiohydrolases, CBHI and CBHII (Shoemaker et al., *Bio/Technology* 1:691–696 (1983); Teeri et al, *Bio/Technology* 1:696–699 (1983); Teeri et al., *Gene* 51:43–52 (1987)) and two endoglucanases, EGI and EGIEI (Penttilä et al. *Gene* 45:253–263 (1986); Van Arsdell et al. *Bio/Technology* 5:60–64 (1987); Saloheimo et al., *Gene* 63:11–21 (1988)) have been isolated from *T. reesei*. The analysis of the gene sequence confirms the protein domain structure (Abuja et al. *Biochem. Biophys. Res. Commun.* 156:180–185 (1988)). The domains of *T. reesei* CBHI and CBHII (Tomme et al., *Eur. J. Biochem.* 170:575–581 (1898)) and EGIH (Ståhlberg et al., *Eur. J. Biochem.* 173:179–183 (1988)) and *Cellulomonas fimi* cellulases (Gilkes et al, *J. Biol. Chem.* 263:10401–10407 (1988)) can be separated proteolytically, but there are no reports concerning *T. reesei* EGI.

A need exists for recombinantly-produced shortened EGI proteins that possess the catalytic activity of EGI. First, a source for recombinant EGI is more cost-effective than isolating the enzyme from the native source. Because *T. reesei* produces a mixture of cellulases, the expression of cloned cDNA in an alternative host, such as *S. cerevisiae*, is highly desired when production of only this cellulase is wanted. Second, a cost-effective source for recombinant EGI allows the industrial utilization of EGI in applications wherein it is desired to add EGI to an in vitro process or to add additional EGI to a mixture of cellulases. Shortened coding sequences have an advantage over longer coding sequences for production by recombinant DNA methods as a peptide containing fewer amino acids is more efficiently produced (for example, more total enzyme activity per total host protein) by a recombinant host than a longer peptide.

SUMMARY OF THE INVENTION

Recognizing the need for recombinant forms of cellulases and cognizant of the lack of understand of EGI in particular, the inventors investigated the biochemical structure of EGI as produced by recombinant hosts. These studies have culminated in the identification of shortened recombinant forms of EGI that possess either the catalytic activity of EGI, or the immunological reactivity of EGI or both.

Thus, this invention is directed to 3'-end deleted EGI cDNAs.

The invention is further directed to vectors capable of expressing the 3'-end deleted EGI cDNAs of the invention.

The invention is further directed to hosts transformed with vectors capable of expressing the 3'-end deleted EGI cDNAs of the invention.

The invention is further directed to methods for the recombinant production of 3'-end deleted EGI protein.

The invention is further directed to 3'-end deleted EGI protein.

The invention is further directed to use of the 3'-end deleted EGI protein.

BRIEF DESCRIPTION OF THE FIGURES

FIG. 2A–2C shows the primary structure of the egl1 gene and EGI protein as determined by sequencing the chromosomal gene and the corresponding cDNA, taken from Penttil ä et al., *Gene* 45:253–263 (1986), incorporated herein fully by reference. Introns are shown in small letters and the suggested splicing signals within the introns are underlined. The cleavage sites for the restriction enzymes KpnI, PstI, SacI, and XhoI are shown. The N-terminal signal sequence preceding the mature protein is underlined, and potential N-glycosylation sites are marked with asterisks. The chromosomal gene was sequenced by the dideoxy method of Sanger et al., *Proc. Natl. Acad. USA* 74:5463–5467 (1977) using restriction fragments cloned in M13mp or pUC vectors. For sequencing from double-stranded pUC vectors, 1 µg of purified plasmid was denatured in 0.4M NaOH at room temperature for 5 min at a concentration of 100 ng/µl. $1.5 \times 10^{-4}$ $A^{260}$ units of sequencing or reverse sequencing primer (Amersham) was added and the mixture was precipitated with ethanol. After washing, the pellet was resuspended in 14 mM Tris-Cl, pH 8, 7 mM MgCl$_2$, and the sequencing reactions were carried out at 37° C. Computer analysis of sequence date was according to the programs of Queen and Korn, *Nucl. Acids Res.* 12:581–599 (1984).

FIG. 6A shows Western blot analysis of proteins produced by yeast strains containing deleted EGI cDNA. EGI was expressed under the control of the yeast ADHI promoter. Immunodetection was done with Mab EI-2, diluted 1:2500. EI, 30 ng of purified EGI; C, yeast strain with full length cDNA; V, yeast strain containing pAAH5; d2–d10, yeast strains containing deleted EGI cDNAs; A, culture medium concentrated from 4.5 ml and treated with PNGase F; (FIG. 6B), cytoplasmic fraction from the cells, collected from 750 µl of stationary phase yeast culture, (FIG. 6C), membrane fraction from the yeast cells, collected from 125 µl or from 300 µl (d6 and d8) of stationary phase yeast culture.

DETAILED DESCRIPTION OF THE PREFERRED EMBODIMENTS

DEFINITIONS

Figure 1:
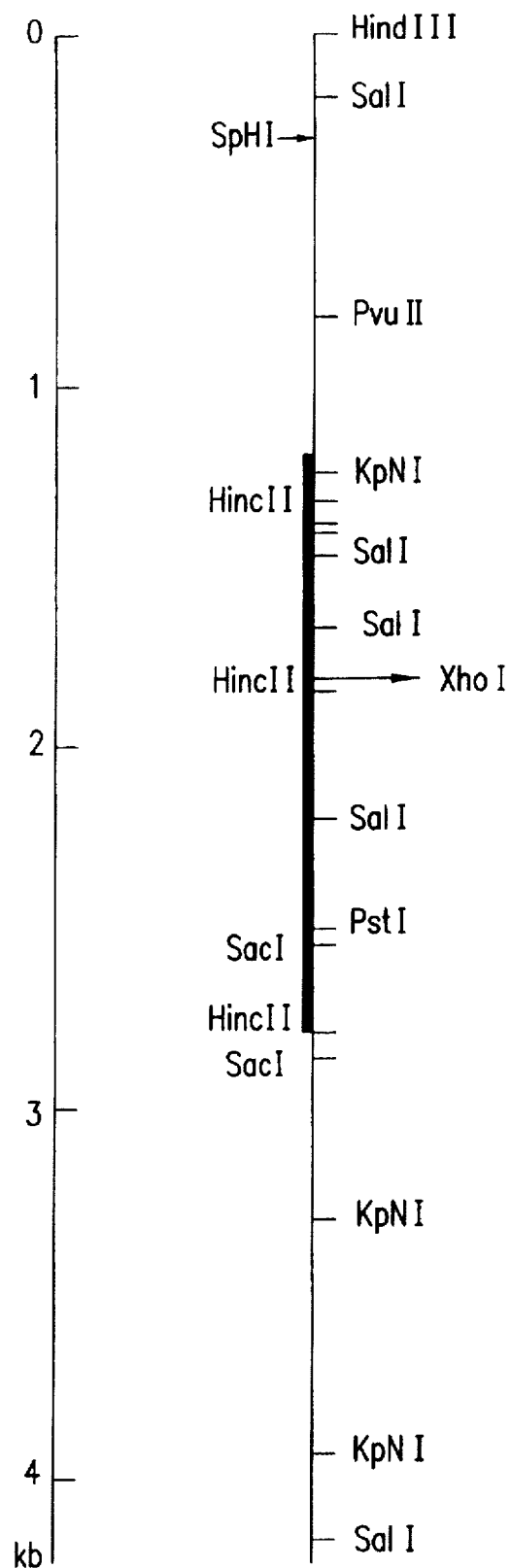
FIG. 1 shows the restriction map of *T. reesei* endoglucanase I (EGI) chromosomal gene. The coding region is marked with thickened line.

In the description that follows, a number of terms used in recombinant DNA (rDNA) technology are extensively utilized. In order to provide a clear and consistent understanding of the specification and claims, including the scope to be given such terms, the following definitions are provided.

Gene. A DNA sequence containing a template for a RNA polymersse. The RNA transcribed from a gene may or may not code for a protein. RNA that codes for a protein is termed messenger RNA (mRNA) and, in eukaryotes, is transcribed by RNA polymerase II. However, a gene containing a RNA polymerase II template wherein a RNA sequence is transcribed which has a sequence complementary to that of a specific mRNA but is not normally translated may also be constructed. Such a gene construct is herein termed an "antisense RNA gene" and such a RNA transcript is termed an "antisense RNA." Antisense RNAs are not normally translatable due to the presence of translational stop codons in the antisense RNA sequence.

A "complementary DNA" or "cDNA" gene includes recombinant genes synthesized by reverse transcription of mRNA lacking intervening sequences (introns).

Cloning vehicle. A plasmid or phage DNA or other DNA sequence which is able to replicate autonomously in a host cell, and which is characterized by one or a small number of endonuclease recognition sites at which such DNA sequences may be cut in a determinable fashion without loss of an essential biological function of the vehicle, and into which DNA may be spliced in order to bring about its replication and cloning. The cloning vehicle may further contain a marker suitable for use in the identification of cells transformed with the cloning vehicle. Markers, for example, are tetracycline resistance or ampicillin resistance. The word "vector" is sometimes used for "cloning vehicle."

Expression vehicle. A vehicle or vector similar to a cloning vehicle but which is capable of expressing a gene which has been cloned into it, after transformation into a host. The cloned gene is usually placed under the control of (i.e., operably linked to) certain control sequences such as promoter sequences. Expression control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Host. A host is a cell, prokaryotic or eukaryotic, that is utilized as the recepient and carrier of recombinant material.

Eukaryotic host. A "eukaryotic host" may be any cell from a eukaryotic organism, including, for example, animal, plant, fungi and yeast.

Functional Derivative. A "functional derivative" of a EGI sequence, either protein or nucleic acid, is a molecule that possesses a biological activity (either functional or structural) that is substantially similar to a biological activity of non-recombinant EGI protein or nucleic acid.

The biological activity of the EGI enzyme is its enzymatic activity or its antigenic determinants (epitopes). A functional derivative of EGI retains either the enzymatic activity of EGI or at least one antigenic determinant of EGI or both enzymatic activity and at least one antigenic determinant of EGI. The EGI enzyme functional derivative of the invention may or may not be operably linked to the EGI secretion signal or functional derivatives thereof. The antigenic epitopes for antibodies against EGI have been mapped (Aho et al., *Eur. J. Biochem.* 200:643–649 (1991)).

The biological activity of the EGI secretion signal is its ability to direct the secretion of peptides to which it is operably linked. A functional derivative of the EGI secretion signal retains the ability to direct secretion of peptides to which it is operably linked.

The biological activity of EGI nucleic acid is a nucleic acid sequence that is sufficient to encode a the EGI functional derivatives of the invention, such as enzymatic EGI functional derivatives, antigenic EGI functional derivatives or EGI secretion signal functional derivatives. A functional derivative of EGI-encoding nucleic acid may or may not include intron sequences, depending upon the ability of the desired host to recognize and remove such sequences.

A functional derivative of EGI protein may or may not contain post-translational modifications such as covalently linked carbohydrate, depending on the necessity of such modifications for the performance of a specific function. The term "functional derivative" is intended to include the "fragments," "variants," "analogues," or "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art.

Fragment. A "fragment" of a molecule such as EGI protein or nucleic acid is meant to refer to any portion or the native EGI amino acid or nucleotide genetic sequence, and in particular the functional derivatives of the invention.

Variant or Analog. A "variant" or "analog" of EGI protein or nucleic acid is meant to refer to a molecule substantially similar in structure and biological activity to either the native EGI molecule, or to a fragment thereof, such as that encoded by alleles.

DESCRIPTION OF THE PREFERRED EMBODIMENTS a. Cloning of Shortened EGI Genetic Sequences

The process for genetically engineering the shortened EGI protein sequences, according to the invention, is facilitated through the isolation and partial sequencing of pure EGI protein and by the cloning of genetic sequences which are capable of encoding the EGI protein and through the expression of such genetic sequences. As used herein, the term "genetic sequences" is intended to refer to a nucleic acid molecule (preferably DNA). Genetic sequences which are capable of encoding EGI protein are derived from a variety of sources. These sources include genomic DNA, cDNA, synthetic DNA, and combinations thereof. The preferred source of the EGI genomic DNA is a *T. reesei* genomic library. The preferred source of the EGI cDNA is a cDNA library prepared form mRNA of *T. reesei* grown in cellulase inducing conditions.

The EGI protein recombinant cDNA of the invention will not include naturally occurring introns if the cDNA was made using mature EGI mRNA as a template. The EGI protein genomic DNA of the invention may or may not include naturally occurring introns. Moreover, such genomic DNA may be obtained in association with the 5' promoter region of the EGI protein gene sequences and/or with the 3' transcriptional termination region. Further, such genomic DNA may be obtained in association with the genetic sequences which encode the 5' non-translated region of the EGI protein mRNA and/or with the genetic sequences which encode the 3' non-translated region. To the extent that a host cell can recognize the transcriptional and/or translational regulatory signals associated with the expression of the MRNA and protein, then the 5' and/or 3' non-transcribed regions of the native gene, and/or, the 5' and/or 3' non-translated regions of the mRNA, may be retained and employed for transcriptional and translational regulation. EGI protein genomic DNA can be extracted and purified from any host cell, especially a fungal host, which naturally expresses EGI protein by means well known in the art (for example, see *Guide to Molecular Cloning Techniques*, S. L. Berger et al., eds., Academic Press (1987). Preferably, the mRNA preparation used will be enriched in mRNA coding for EGI protein, either naturally, by isolation from cells which are producing large amounts of the protein, or in vitro, by techniques commonly used to enrich mRNA preparations for specific sequences, such as sucrose gradient centrifugation, or both.

For cloning into a vector, such suitable DNA preparations (either genomic DNA or cDNA) are randomly sheared or enzymatically cleaved, respectively, and ligated into appropriate vectors to form a recombinant gene (either genomic or cDNA) library.

A DNA sequence encoding EGI protein or its functional derivatives may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., (Maniatis, T. et al., *Molecular Cloning (A Laboratory Manual)*, Cold Spring Harbor Laboratory, second edition, 1988) and are well known in the art.

Libraries containing sequences coding for EGI may be screened and a sequence coding for EGI identified by any means which specifically selects for a sequence coding for EGI such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated EGI protein product produced by the host containing the clone.

Antibodies specific for EGI protein, that can be used to identify clones to this protein can be raised against purified forms of this enzyme. Oligonucleotide probes designed from knowledge of the amino acid sequence of the EGI protein can be used to identify DNA clones to this protein. The sequence of amino acid residues in a peptide is designated herein either through the use of their commonly employed three-letter designations or by their single-letter designations. A listing of these three-letter and one-letter designations may be found in textbooks such as *Biochemistry*, Lehninger, A., Worth Publishers, New York, N.Y. (1970). When the amino acid sequence is listed horizontally, unless otherwise stated, the amino terminus is intended to be on the left end and the carboxy terminus is intended to be at the right end.

Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., in: *Molecular Biology of the Gene*, 3rd Ed., W. A. Benjamin, Inc., Menlo Park, Calif. (1977)), one or more different oligonucleotides can be identified from the amino acid sequence, each of which would be capable of encoding EGI. The probability that a particular oligonucleotide will, in fact, constitute an actual EGI protein encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1-12 (1985). Using the "codon usage rules" of Lathe, a single oligonucleotide sequence, or a set of oligonucleotide sequences, that contain a theoretical "most probable" nucleotide sequence capable of encoding the EGI protein sequences is identified.

The suitable oligonucleotide, or set of oligonucleotides, which is capable of encoding a fragment of a EGI gene (or which is complementary to such an oligonucleotide, or set of oligonucleotides) may be synthesized by means well known in the art (see, for example, *Synthesis and Application of DNA and RNA*, S. A. Narang, ed., 1987, Academic Press, San Diego, Calif.) and employed as a probe to identify and isolate a cloned EGI gene by techniques known in the art. Techniques of nucleic acid hybridization and clone identification are disclosed by Maniatis, T., et al., in: *Molecular Cloning, A Laboratory Manual*, Cold Spring Harbor Laboratories, Cold Spring Harbor, N.Y. (1982)), and by Hames, B. D., et al., in: *Nucleic Acid Hybridization, A Practical Approach*, IRL Press, Washington, D.C. (1985)), which references are herein incorporated by reference. Those members of the above-described gene library which are found to be capable of such hybridization are then analyzed to determine the extent and nature of EGI encoding sequences which they contain.

To facilitate the detection of a desired EGI protein DNA encoding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radio-active labels, such as $^{32}P$, $^{3}H$, $^{14}C$, $^{35}S$, $^{125}I$, or the like. Any radioactive label may be employed which provides for an adequate signal and has a sufficient half-life. If single stranded, the oligonucleotide may be radioactively labelled using kinase reactions.

Alternatively, polynucleotides are also useful as nucleic acid hybridization probes when labeled with a non-radioactive marker such as biotin, an enzyme or a fluorescent group. See, for example, Leary, J. J. et al., *Proc. Natl. Acad. Sci. USA* 80:4045 (1983); Renz, M. et al., *Nucl. Acids Res.* 12:3435 (1984); and Renz, M., *EMBO J.* 6:817 (1983).

Thus, in summary, the actual identification of EGI protein sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing a EGI gene.

In an alternative way of cloning a EGI gene, a library is prepared using an expression vector, by cloning DNA or, more preferably cDNA prepared from a cell capable of expressing EGI protein into an expression vector. The library is then screened for members which express EGI protein, for example, by screening the library with antibodies to the protein.

The above discussed methods are, therefore, capable of identifying genetic sequences which are capable of encoding EGI protein or fragments of this protein. In order to further characterize such genetic sequences, and, in order to produce the recombinant protein, it is desirable to express the proteins which these sequences encode. Such expression identifies those clones which express proteins possessing characteristics of EGI protein. Such characteristics may include the ability to specifically bind EGI protein antibody, the ability to elicit the production of antibody which are capable of binding to EGI protein, the ability to provide EGI protein enzymatic activity to a cell, and the ability to provide a EGI protein-function to a recipient cell, among others.

The full-length EGI DNA sequence may be shortened by means known in the art to produce the shortened EGI sequences of the invention. For example, restriction digestion may be utilized to cleave the full-length sequence at a desired location. Alternatively, or in addition, nucleases that cleave from the 3'-end of a DNA molecule may be used to digest a certain sequence to a shortened form, the desired length then being identified and purified by gel electrophoresis and DNA sequencing. Such nucleases include, for example, Exonuclease II and Bal31. Other nucleases have been disclose by Maniatis, T. (Maniatis, T. et al, *Molecular Cloning (A Laboratory Manual)*, Cold Spring Harbor Laboratory, second edition, 1988) and are well known in the art.

Accordingly, by the methods described herein, functional derivatives of EGI may be prepared, such as, for example, those encoded by (amino acid numbers refer to amino acids shown on FIG. 2A-2C, where amino acids 1-459 encode the full-length EGI):

| Amino acid No. (with signal sequence) | Amino acid No. (without signal sequence) |
|---|---|
| 1-458 | 23-458 |
| 1-457 | 23-457 |
| 1-456 | 23-456 |
| 1-455 | 23-455 |
| 1-454 | 23-454 |
| 1-453 | 23-453 |

-continued

| Amino acid No.<br>(with signal<br>sequence) | Amino acid No.<br>(without signal<br>sequence) |
|---|---|
| 1-452 | 23-452 |
| 1-451 | 23-451 |
| 1-450 | 23-450 |
| 1-449 | 23-449 |
| 1-448 | 23-448 |
| 1-447 | 23-447 |
| 1-446 | 23-446 |
| 1-445 | 23-445 |
| 1-444 | 23-444 |
| 1-443 | 23-443 |
| 1-442 | 23-442 |
| 1-441 | 23-441 |
| 1-440 | 23-440 |
| 1-439 | 23-439 |
| 1-438 | 23-438 |
| 1-437 | 23-437 |
| 1-436 | 23-436 |
| 1-435 | 23-435 |
| 1-434 | 23-434 |
| 1-433 | 23-433 |
| 1-432 | 23-432 |
| 1-431 | 23-431 |
| 1-430 | 23-430 |
| 1-429 | 23-429 |
| 1-428 | 23-428 |
| 1-427 | 23-427 |
| 1-426 | 23-426 |
| 1-425 | 23-425 |
| 1-424 | 23-424 |
| 1-423 | 23-423 |
| 1-422 | 23-422 |
| 1-421 | 23-421 |
| 1-420 | 23-420 |
| 1-419 | 23-419 |
| 1-418 | 23-418 |
| 1-417 | 23-417 |
| 1-416 | 23-416 |
| 1-415 | 23-415 |
| 1-414 | 23-414 |
| 1-413 | 23-413 |
| 1-412 | 23-412 |
| 1-411 | 23-411 |
| 1-410 | 23-410 |
| 1-409 | 23-409 |
| 1-408 | 23-408 |
| 1-407 | 23-407 |
| 1-406 | 23-406 |
| 1-405 | 23-405 |
| 1-404 | 23-404 |
| 1-403 | 23-403 |
| 1-402 | 23-402 |
| 1-401 | 23-401 |
| 1-400 | 23-400 |
| 1-399 | 23-399 |
| 1-398 | 23-398 |
| 1-397 | 23-397 |
| 1-396 | 23-396 |

A skilled artisan would recognize that, the EGI signal sequence (MetAlaProSerValThrLeuProLeuThrThrAlaIle-LeuAlaIleAlaArgLeuValAlaAla [SEQ ID No. 3]) being amino acids 1–22 of FIG. 2A, such sequence could be removed without altering the biological activity, and especially the enzymatic activity, of the remaining coding sequence.

b. Expression of EGI Protein and its Functional Derivatives

To express EGI protein and/or its active derivatives, transcriptional and translational signals recognizable by an appropriate host are necessary. The cloned EGI protein encoding sequences, obtained through the methods described above, and preferably in a double-stranded form, may be operably linked to sequences controlling transcriptional expression in an expression vector, and introduced into a host cell, either prokaryote or eukaryote, to produce recombinant EGI protein or a functional derivative thereof. Depending upon which strand of the EGI protein encoding sequence is operably linked to the sequences controlling transcriptional expression, it is also possible to express EGI protein antisense RNA or a functional derivative thereof.

Expression of the EGI protein in different hosts may result in different post-translational modifications which may alter the properties of the protein. Preferably, the present invention encompasses the expression of the EGI protein or a functional derivative thereof, in eukaryotic cells, and especially yeast and plant or other eukaryotic cells. Especially preferred eukaryotic hosts are yeast cells such as laboratory strains of Saccharomyces cerevisiae. Such cells provide post-translational modifications to recombinant EGI protein which include folding at sites similar or identical to that found for the native protein.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a EGI protein encoding sequence and a promoter region sequence linked to the 5' end of the encoding sequence) are said to be operably linked if induction of promoter function results in the transcription of the EGI protein encoding sequence mRNA and if the nature of the linkage between the two DNA sequences does not (1) result in the introduction of a frame-shift mutation, (2) interfere with the ability of the expression regulatory sequences to direct the expression of the EGI protein, antisense RNA, or (3) interfere with the ability of the EGI protein template to be transcribed by the promoter region sequence. Thus, a promoter region would be operably linked to a DNA sequence if the promoter was capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene. Such transcriptional control sequences may also include enhancer sequences or upstream activator sequences, as desired.

Expression of the EGI protein in eukaryotic hosts requires the use of regulatory regions functional in such hosts, and preferably eukaryotic regulatory systems. A wide variety of transcriptional and translational regulatory sequences can be employed, depending upon the nature of the eukaryotic host. Preferably, these regulatory signals are associated with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

Promoters from heterologous mammalian genes which encode a mRNA product capable of translation are preferred, and especially, strong promoters such as the promoter for actin, collagen, myosin, etc., can be employed provided they also function as promoters in the host cell. Preferred strong eukaryotic promoters include the yeast GAL4 gene promoter (Johnston, S. A., et al., *Proc. Natl. Acad. Sci. (USA)* 79:6971–6975 (1982); Silver, P. A., et al, *Proc. Natl. Acad. Sci. (USA)* 81:5951–5955 (1984)) or a glycolytic gene promoter may be used, such as that for phosphoglycerolkinase (PGK). In yeast, the constitutive alcohol dehydrogenase (ADHI) promoter (Ammerer, G. *Meth. Enzymol.* 101C: 192–201 (1983); Aho, *FEBS Lett.* 291:45–49 (1991) and MEL1 (Suominen, P. L. Dissertation, Univ. Helsinki, Helskink, Finland, 1988) promoter also can be used. In plants, the plant promoters from ribulase bisphosphate carboxylase can be used. 35S promoter from CaMV or promoters derived from Ti plasmid of *Agrobacter tumefaciens* can be used in plants also.

As is widely known, translation of eukaryotic mRNA is initiated at the codon which encodes the first methionine. For this reason, it is preferable to ensure that the linkage between a eukaryotic promoter and a DNA sequence which encodes the EGI protein, or a functional derivative thereof, does not contain any intervening codons which are capable of encoding a methionine. The presence of such codons results either in a formation of a fusion protein (if the AUG codon is in the same reading frame as EGI protein encoding DNA sequence) or a frame-shift mutation (if the AUG codon is not in the same reading frame as the EGI protein encoding sequence).

If desired, a fusion product of the EGI protein may be constructed. For example, the sequence coding for EGI protein may be linked to a signal sequence which will allow secretion of the protein from, or the compartmentalization of the protein in, a particular host. Such signal sequences may be designed with or without specific protease sites such that the signal peptide sequence is amenable to subsequent removal in a preferred embodiment, the native signal sequence of EGI is used, or a functional derivative of that sequence that retains the ability to direct the secretion of the peptide that is operably linked to it.

Transcriptional initiation regulatory signals can be selected which allow for repression or activation, so that expression of the operably linked genes can be modulated. Of interest are regulatory signals which are temperature-sensitive so that by varying the temperature, expression can be repressed or initiated, or are subject to chemical regulation, e.g., metabolite. Also of interest are constructs wherein both the EGI protein mRNA and antisense RNA are provided in a transcribable form but with different promoters or other transcriptional regulatory elements such that induction of EGI protein mRNA expression is accompanied by repression of antisense RNA expression, and/or, repression of EGI protein mRNA expression is accompanied by induction of antisense RNA expression. Translational signals are not necessary when it is desired to express EGI protein antisense RNA sequences.

If desired, the non-transcribed and/or non-translated regions 3' to the sequence coding for EGI protein can be obtained by the above-described cloning methods. The 3'-non-transcribed region may be retained for its transcriptional termination regulatory sequence elements; the 3-non-translated region may be retained for its translational termination regulatory sequence elements, or for those elements which direct polyadenylation in eukaryotic cells. Where the native expression control sequences signals do not function satisfactorily in the host cell, then sequences functional in the host cell may be substituted.

The vectors of the invention may further comprise other operably linked regulatory elements such as DNA elements which confer tissue or cell-type specific expression on an operably linked gene.

If the EGI protein encoding sequence and an operably linked promoter is introduced into a recipient eukaryotic cell as a non-replicating DNA (or RNA) molecule, the expression of the EGI protein may occur through the transient expression of the introduced sequence. Such a non-replicating DNA (or RNA) molecule may be a linear molecule or, more preferably, a closed covalent circular molecule which is incapable of autonomous replication.

In a preferred embodiment, genetically stable transformants may be constructed with vector systems, or transformation systems, whereby EGI protein DNA is integrated into the host chromosome or into the yeast as an autonomically replicating plasmid. Such integration may occur de novo within the cell or, in a most preferred embodiment, be assisted by transformation with a vector which functionally inserts itself into the host chromosome, for example, with retroviral vectors, transposons or other DNA elements which promote integration of DNA sequences in chromosomes. A vector is employed which is capable of integrating the desired gene sequences into a mammalian host cell chromosome.

Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transfection. For example, use of the yeast MEL1 gene as a stable selection marker gene is presented in U.S. Pat. No. 5,055,401.

In another embodiment, the introduced sequence is incorporated into a plasmid or viral vector capable of autonomous replication in the recipient host. Any of a wide variety of vectors may be employed for this purpose, as outlined below.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40; in plants, plant CAMV (Caliiflower Mosaic Virus); and, in yeast, plasmids containing the 2-micron circle, etc., or their derivatives. Such plasmids are well known in the art (Botstein, D., et al., *Miami Wntr. Symp.* 19:265–274 (1982); Broach, J. R., in: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bollon, D. P., et al, *J. Clin. Hematol. Oncol.* 10:39–48 (1980); Maniatis, T., In: *Cell Biology: A Comprehensive Treatise*, Vol. 3, Gene Expression, Academic Press, N.Y., pp. 563–608 (1980)), and are commercially available.

Once the vector or DNA sequence containing the construct(s) is prepared for expression, the DNA construct (s) is introduced into an appropriate host cell by any of a variety of suitable means, including transfection. After the introduction of the vector, recipient cells are grown in a selective medium, which selects for the growth of vector-containing cells. Expression of the cloned gene sequence(s) results in the production of the EGI protein, or in the production of a fragment of this protein. This expression can take place in a continuous manner in the transformed cells, or in a controlled manner, for example, expression which follows induction.

The expressed protein is isolated and purified in accordance with conventional conditions, such as extraction, precipitation, chromatography, affinity chromatography, electrophoresis, or the like. Methods for the purification of native EGI are known in the art Niku-Pasvola et al. *Biochem. J.* 231:75–81 (1985)). The shortened EGI proteins of the invention retain at least one biological activity of EGI, such as enzymatic activity or an antigenic determinant. Therefore, the shortened EGI proteins of the invention may be extracted and purified utilizing the desired biological activity to monitor such extraction or purification.

The EGI protein DNA encoding sequences, obtained through the methods above, will provide sequences which, by definition, encode EGI protein and which may then be used to obtain EGI protein antisense RNA genetic sequences as the antisense RNA sequence will be that sequence found on the opposite, complementary strand of the strand transcribing the protein's mRNA. An expression vector may be constructed which contains a DNA sequence operably linked to a promoter wherein such DNA sequence expresses the EGI antisense RNA sequence. Transformation with this vector results in a host capable of expression of a EGI antisense RNA in the transformed cell. Preferably such expression occurs in a regulated manner wherein it may be induced and/or repressed as desired. Most preferably, when expressed, antisense EGI RNA interacts with an endogenous EGI DNA or RNA in a manner which inhibits or represses transcription and/or translation of the EGI protein gene and/or mRNA in a highly specific manner. Use of antisense RNA probes to block gene expression is discussed in Lichtenstein, C., *Nature* 333:801–802 (1988).

To construct the shortened EGI proteins of the invention, site-directed mutagenesis may be performed using techniques known in the art, such as the in vitro mutagenesis kit of Amersham, UK, and the mutations confirmed by DNA sequencing. Yeast transformation are carried out also accordingly to techniques known in the art, for example, Keszenman-Pereyra and Hieda (K. Keszenman-Pereyra and K. Hieda, *Curr. Genet.* 13:21–23 (1988). The transformants may by grown in shake flasks in 50 ml of YEP-D (F. Sherman et al., "Methods in yeast genetics. A laboratory manual," Cold Springs Harbor Laboratory, (1983). Aliquots (for example 2 ml) may be withdrawn at appropriate intervals and used to measure cell density ($A^{600}$ nm) and enzyme activity.

Enzyme activities may be determined spectrophotometrically and by discontinuous assay, using 4-methylumbelliferyl lactoside as substrate ((S)=0.25 mM, pH 5.0, t=50° C.) (H. Van Tilbeurgh et al, *Methods EnzymoL* 160.45–59 (1988)). Quantification of the forms EGI in the yeast growth media may be performed as follows: 4 μl of culture medium is spotted on a nitrocellulose filter which is blocked as for Western blotting, treated with polyclonal rabbit antiserum against EGI (M. Nummi et al., *Biochem. J.* 215:677–683 (1983)) or a monoclonal antibody against the EGI C-terminal part (S. Aho et al., *Fourth Nordic Symposiun on Gene Technology in Basic and Applied Research, Feb.* 10–14, *Abstract*, p. 77 (1990), Aho et al., *Eur. J. Biochem.* 200:643–649 (1991)), and finally with 35S-labelled protein A, whereafter the membrane is cut into pieces and the radioactivity of each dot counted in Triton-cocktail in a scintillation counter. The specific radioactivity is estimated from a standard curve (cpm/protein concentration) obtained by the same procedure using purified native EGI from *T. reesei*.

For the rapid screening of microorganisms producing and secreting endo-1,4-β-glucanase plate assays may be used to detect enzymatic activity. The substrate polymer may be incorporated into the basal growth medium and the production of hydrolases indicated by the clear zones of dissolved substrate around the colonies. Carboxymethylcellulose (CMC) and hydroxyethylcellulose (HEC), the substituted polymeric analogs of cellulose are generally used (Penttill a et al, *Yeast* 3:175–185 (1987)). In the medium with CMC or β-glucan the detection of cellulases is accomplished by staining the residual substrate by Congo red (Wood, P. J., *Carbohydr. Res.* 85:271–287 (1980)). When soluble HEC covalently dyed with OBR is mixed to agar nutrient media, the formation of pale clearing zones of the dissolved substrate around the growing colonies indicates the production of endoglucanases (Farkas et al, *FEMS Microbiol. Lett.* 28:137–140 (1985)). The yeast strains producing individual cellulases from the cloned cDNAs showed that endoglucanases possess considerable activity against hydroxyethylcellulose but cellobiohydrolases did not solubilize this substrate. The yeast endogenous glucanases did not show any activity against OBR-HEC. This method is useful for screening a large number of yeast colonies for the increased EGI production after mutagenesis (Arffman et al, *Yeast* 6:S438 (1990)).

As demonstrated herein, the truncated EGI proteins lacking the Thr-Ser-rich B-region, encoded by d5 to d9 (see Examples and FIG. 5), were found in the cell membrane fraction but only the EGI proteins containing the Thr-Ser-rich region or part of it are found in the soluble fraction of yeast cells. Because the whole cells are fractionated, the soluble fraction contained b6th the cytoplasmic and periplasmic soluble proteins. Proteins encoded by cDNA deletions d5, d7 and d8 (FIG. 5) are found secreted into the culture medium. This suggests that the secretion of *T. reesei* endoglucanase I from *S. cerevisiae* does not involve any specific linear amino acid sequence in addition to the amino terminal signal sequence, but most probably results from the favorable folding of protein. The secretion of the truncated proteins did not either correlate to the number of putative N-glycosylation sites on each truncated protein.

*Cellulomonas fimi* cellulases show considerable conservation of functional domains with *T. reesei* cellulases (Knowles et al., *Trends Biotechnol.* 5:255–261 (1987)). The gene regions coding for the catalytic domains ("core" region) of the exoglucanase (Exg) and the endoglucanase (EngA) has been fused and expressed in *E. coli* (Warren et al. *Gene* 61:421–427 (1987)). The active bifunctional fusion protein was obtained; even part of the endoglucanase "core" region became deleted as a result of the gene fusion method used. The intact core region of *T. reesei* EGI is necessary for the enzymatic activity. Because the putative active site is located about 200 amino acids away from the hinge region, the loss of activity after the removal of the 13 COOH-terminal amino acids of the core region can be due to the improper folding.

c. Construction and Identification of Antibodies to EGI Protein

In the following description, reference will be made to various methodologies well-known to those skilled in the art of immunology. Standard reference works setting forth the general principles of immunology include the work of Catty, D. (*Antibodies, A Practical Approach*, Vol. 1, IRL Press, Washington, D.C. (1988)); Klein, J. (*Immunology: The Science of Cell-Noncell Discrimination*, John Wiley & Sons, New York (1982)); Kennett, R., et al. in *Monoclonal Antibodies, Hybridoma: A New Dimension in Biological Analyses*, Plenum Press, New York (1980)); Campbell, A. ("Monoclonal Antibody Technology," in: *Laboratory Techniques in Biochemistry and Molecular Biology*, Volume 13 (Burdon, R., et al., eds.), Elsevier, Amsterdam (1984)); and Eisen, H. N., in: *Microbiology*, 3rd Ed. (Davis, B. D., et al., Harper & Row, Philadelphia (1980)).

An antibody is said to be "capable of binding" a molecule if it is capable of specifically reacting with the molecule to thereby bind the molecule to the antibody. The term "epitope" is meant to refer to that portion of a hapten which can be recognized and bound by an antibody. An antigen may have one, or more than one epitope. An "antigen" is capable of inducing an animal to produce antibody capable of binding to an epitope of that antigen. The specific reaction referred to above is meant to indicate that the antigen will react, in a highly selective manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al, *J. NucL Med.* 24:316–325 (1983)).

The antibodies of the present invention are prepared by any of a variety of methods. Preferably, purified EGI protein, or a fragment thereof, is administered to an animal in order to induce the production of sera containing polyclonal antibodies that are capable of binding EGI. Cells expressing EGI protein, or a fragment thereof, or, a mixture of proteins containing EGI or such fragments, can also be administered to an animal in order to induce the production of sera containing polyclonal antibodies, some of which will be capable of binding EGI protein. If desired, such EGI antibody may be purified from the other polyclonal antibodies by standard protein purification techniques and especially by affinity chromatography with purified EGI or fragments thereof.

A EGI protein fragment may also be chemically synthesized and purified by HPLC to render it substantially free of contaminants. Such a preparation is then introduced into an animal in order to produce polyclonal antisera of high specific activity.

Monoclonal antibodies can be prepared using hybridoma technology (Kohler et al., *Nature* 256:495 (1975); Kohler et al. *Eur. J. ImmunoL* 6:511 (1976); Kohler et al, *Eur. J. Immunol.* 6:292 (1976); Hammerling et al., in: *Monoclonal Antibodies and T-Cell Hybridomas*, Elsevier, N. Y., pp. 563–681 (1981)). In general, such procedures involve immunizing an animal with EGI protein antigen. The splenocytes of such animals are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Maryland. After fusion, the resulting hybridoma cells are selectively maintained in HAT medium, and then cloned by limiting dilution as described by Wands, J. R., et al. *Gastroenterology* 80:225–232 (1981), which reference is herein incorporated by reference. The hybridoma cells obtained through such a selection are then assayed to identify clones which secrete antibodies capable of binding the EGI protein antigen.

Through application of the above-described methods, additional cell lines capable of producing antibodies which recognize epitopes of the EGI protein can be obtained.

Antibodies against both highly conserved and poorly conserved regions of the EGI protein are useful for the identification of clones expressing the EGI functional derivatives of the invention.

The examples below are for illustrative purposes only and are not deemed to limit the scope of the invention.

EXAMPLES

Methods and materials, unless otherwise described, are described in the dissertation of S. Nitisenprasert, Univ. Helsinki, Helsinki, Finland and in the publication by Mitsuishi et al., *FEBS Lett.* 275:135–138 (1990), both incorporated herein by reference.

Materials and Methods for Examples 1–5

Bacterial and fungal strains, plasmids, and phage. *T. reesei* strain VTT-D-80133, a mutant strain with improved production of cellulolytic enzymes derived from QM 9414 (M. Mandels et al., *Appl. Microbiol* 21:152–154 (1971)) after several successive mutation steps (K. M. H. Nevalainen, *Environ. Microbiol.* 41:595–596 (1981)), was used for isolation of the gene for endoglucanase I (EGI).

*Escherichia coli* strains Q358 and Q359 and the phage λ 1059, used in the construction of the *T. reesei* gene bank were provided by Dr. J. Karn (J. Karn et al., *Proc. Natl. Acad. Sci.*, 77.5172–5176, *Novel bacteriophage cloning vector* (1980)). *E. coli* HB 101 was used as a host in 5 transformation with the plasmid pBR 322. *E. coli* JM 101 and the phage M 13 mp 7 (J. Messing et al., *Nucleic Acid Res.* 9:309–321, "*A System for Shotgun DNA Sequencing*" (1981)) and the plasmids pUC 8 and pUC 9 (J. Vieira and J. Messing, *Gene* 19:259–268 (1982)), used in the dideoxy sequencing, were from the laboratory of F. Sanger. Yeast strains used were *Saccharomyces cerevisiae* OL1 (Mata leu 2–3 leu 2–112 his 3–11 his 3–15 ura 3–251 ura 3–373) (E. Boy-Marcotte and M. Jaquet, "*A Dictyostelium Discoideum DNA Fragment Complements A Saccharomyces Cerevisiae ura3 Mutant*", *Gene* 20:433–440 (1982)) and *S. cerevisiae* MT302-1c (Mata arg 5–6 leu 2–3 leu 2–112 his 3–11 his 3–15 pep 4–3 ade 1) (J. Mellor et al., "*Efficient Synthesis of Enzymatically Active Calf Chymosin in Saccharomyces Cerevisiae*", *Gene* 24:1–14 (A. J. Kingsman & Kingsman)).

A yeast expression vector containing the phosphoglycerokinase CPGK) gene promoter was used for expression of the cDNA copies of cellulase genes in yeast (J. Mellor et al, "*Efficient Synthesis of Enzymatically Active Calf Chymosin in Saccharomyces Cerevisiae*", *Gene* 24:1–14 (A. J. Kingsman & Kingsman)).

Enzymes. Restriction enzymes were purchased from Amersham (UK), Boehringer Mannheim (FDR) and Bethesda Research Laboratories (Gaithersburg, Md.) and used according to the manufacturers' instructions. T4 ligase and the DNA polymerase I large subunit were from Biolabs and the calf intestine phosphatase from Boehringer Mannheim. Reverse transcriptase was from Dr. J. W. Beard (Life Sciences Inc., St. Petersburg, Fla.). Protoplasting enzyme, Zymolyase 60000 was obtained from Kirin Brewery Co., Japan. Klenow fragment of E. coli polymerase I was from Boehringer Mannheim.

General growth media. E. coli HB101 was grown in L-broth. Transformants were selected on L-plates supplemented with 1.5% agar and containing 100 µg/ml ampicillin. The concentration of tetracycline added to L-plates was 10 µg/ml. Complete medium YPG for growth of yeast contained 1% yeast extract, 2% peptone, and 2% glucose. Yeast minimal medium, YMB, contained 0.67% yeast nitrogen base (Difco, Detroit, USA) and 2% sugar Qactose, cellobiose, starch or glucose). The final concentration of amino yeast plates was 2% agar (Difco Bacto Agar). In yeast protoplast plating medium 1.2M sorbitol was added as an osmotic stabilizer. The top agar used in plating the yeast protoplasts for regeneration was prepared as minimal medium but using 3% purified agar (Difco) as a solidifying agent.

All methods unless otherwise specified are as described in Maniatis et al. 1982 (T. Maniatis et al., "*Molecular Cloning: A Laboratory Manual,*" Cold Spring Harbor Laboratory, (New York 1982)).

EXAMPLE 1

Isolation and characterization of the cellulolytic genes from the fungus *T. reesei*

Polyadenylated (polyA⁺) messenger RNA isolated from *T. reesei* mycelia actively producing cellulases directs in the in vitro synthesis—in a rabbit reticulocyte lysate—of a number of large polypeptides that are precipitated by antibody prepared against purified cellulolytic enzymes. Messenger RNA isolated from repressed glucose grown mycelia does not direct the synthesis of these cellulase-specific polypeptides. This difference between induced and repressed populations was used to identify a collection of hybrid λ phages containing *T. reesei* genes strongly expressed during production of cellulolytic enzymes.

For the isolation of cellulase-specific, induced mRNAs *T. reesei* (strain VTT-D-80133) was grown as described by Bailey and Nevalainen (M. J. Bailey et al., "*Induction, Isolation and Testing of Stable Trichoderma Reesei Mutants With Improved Production of Solubilizing Cellulase,*" Enzyme Microb. Technol. 3:153–157 (1981)) except that the medium contained 2% lactose and 2% of a soluble extract of distillers spent grain. Samples taken during cultivation were assayed for activity against dyed Avicel, hydroyethylcellulose (HEC) and for soluble protein (M. J. Bailey et al, "*Induction, Isolation and Testing of Stable Trichoderma Reesei Mutants With Improved Production of Solubilizing Cellulase,*" Enzyme Microb. Technol. 3:153–157 (1981)). Estimation of reducing sugars was by the method of Summer (J. B. Sumner and G. F. Somers, *Laboratory Experiments In Biological Chemistry* 2nd ed. pp. 38–39, Academic Press (New York 1949)).

Cellular RNA from mycelia was isolated by a modification of the method of Ohi and Short (S. Ohi and J. Short, "*A General Procedure for Preparing Messenger RNA from Eukaryotic Cells Without Using Phenol.,*" J. Appl. Microbiol. 2:398–413 (1980)). The frozen mycelia was ground to a fine powder under liquid nitrogen and suspended in a buffer containing 20 mM Tris-HCl (pH 7.6), 0.1M NH₄ 1 mM Mg(OAc)₂, 10 mM Na-iodoacetate, 0.5 mg/ml polyvinylsulfate and 2% Na-dodecyl sulfate (SDS). Following incubation at 37° C. for 30 minutes, insoluble material was removed by centrifugation at 13000 g for 10 minutes.

The poly(A)⁺ fraction was purified by chromatography through an oligo(dT) cellulose column (Bethesda Research Laboratories (H. Aviv and P. Leder, *Proc. Natl. Acad. Sci.* 69:1408–1412 (1972)) and in vitro translation was carried out with a rabbit reticulocyte lysate using ³⁵S-methionine (Amersham International Ltd) (H. R. B. Pelham and R. J. Jackson, *Env. J. Biochem.* 67:247–256 (1976)). Immunoprecipitation was carried out according to Dobberstein (B. Dobberstein et al., *Cell* 17:759–769 (1979)) using antiserum prepared against purified CBH I, CBH II, or EGI, or with the corresponding preimmune serum.

Table 1 shows the molecular weights of proteins precipitated by antiserum against specific cellulases analyzed on 7.5–15% SDS polyacrylamide gels (U. Laemmli, "*Cleavage of Structural Proteins During the Assembly of Bacteriophage T4,*" Nature 227:680–685 (1970)).

TABLE 1

| Antiserum | In vivo | In vitro |
|---|---|---|
| CBH I | 71,000 | 67,000 |
| CBH II | 63,000 | 48,000 |
| EGI | 62,000 | 53,000 |

The construction of the *T. reesei* gene bank was carried out as follows.

Conidia of *Trichodenma reesei* were germinated in a liquid medium containing 1.5% KH₂PO₄, 0.5% (NH₄)₂SO₄, 0.06% MgSO₄•7H₂O, 0.06% CaCl₂, 0.15% proteose peptone, 0.03% urea, 2% sucrose and minimal salts. Cultures were incubated with shaking at 29° C. for about 12 h. The isolation of nuclei was carried out using a slightly modified method of Hautala et al. (J. A. Hautala et al, "*Isolation and Characterization of Nuclei from Neurospora Crassa.,*" J. Bacteriol. 130:704–713 (1977)). DNA was isolated from a crude nuclear pellet obtained by differential centrifugation of homogenized mycelium. The crude nuclear pellet was treated with SDS-amylase solution (100 mM EDTA pH 8.0, 140 mM NaCl, 1% Nadecylsulfate and 3.3% α-amylase obtained from Merck, Darmstadt, FRG) for 1 h at 37° C. Proteinase K (final concentration 0.8% w/v) was then added and incubation was continued for 2 h at 37° C. with gentle shaking. After incubation, cell debris was removed by centrifugation and DNA was precipitated from the supernatant with ethanol. The DNA was then purified by CsCl centrifugation. The chromosomal DNA from *T. reesei* was partially digested with MboI and sized by sucrose density gradient centrifugation. Fifteen-20 kb fragments were ligated to Bam HI-cleaved λ 1050 DNA. In vitro packaging of the recombinant molecules was carried out using packaging extracts prepared by the method of Hohn as described by Maniatis et al (T. Maniatis et al, "*Molecular Cloning: A Laboratory Manual,*" Cold Spring Harbor Laboratory, (New York 1982)).

Recombinant phages were transferred from the agar to nitrocellulose filters (Schleicher & Schuill, BA 85) as described by Benton and Davis (W. D. Benton and R. W. Davis, "*Screening λgt Recombinant Clones by Hybridization to Single Plaques In Situ,*" Science 196:180–182 (1977)). cDNAs made from induced MRNA (described earlier) and from mRNA isolated from fungus grown in the presence of glucose were used as probes. cDNA first strand synthesis was carried out by the procedure of Efstradiatis et al (A. Efstradiatis et al, "*Enzymatic In Vitro Synthesis of Globi Genes,*" Cell 7:279–288 (1976)) but using 10 µCi of ³²PaATP per 50 µl reaction. The in situ plaque hybridization was carried out according to Maniatis et al (T. Maniatis et al, "*Molecular Cloning: A Laboratory Manual,*" Cold Spring Harbor Laboratory, (New York 1982)). Hybridization was detected by autoradiography of the filters on Kodak X-OMAT film. Positive plaques were picked into 1 ml of SM (T. Maniatis et al., "Molecular Cloning: A Laboratory Manual," Cold Spring Harbor Laboratory, (New York 1982)) and a drop of chloroform and stored at −4° C.

Hybrid phage hybridizing only to cDNA made with induced MRNA containing cellulase coding sequences were purified extensively and retested by hybridization to both probes. A number of different hybrid clones that hybridized strongly to the induced cellulase probe were identified and selected for further analysis.

The hybrid phages containing genes induced when the fungus produces cellulases were first grouped according to their restriction enzyme patterns. Then the particular cellulase gene in each group was identified by hybrid selection of messenger RNA.

DBM paper was obtained from Schleicher and Schuill (Keene, N.H.) and activated according to the maker's instructions. Binding of DNA to the activated paper and RNA hybridization and elution was carried out according to Maniatis et al (T. Maniatis et al., "Molecular Cloning: A Laboratory Manual," Cold Spring Harbor Laboratory, (New York 1982)). RNA was translated with a rabbit reticulocyte lysate supplied by Amersham International Ltd. and the proteins produced were labeled with $^{35}$S-methionine. The proteins were analyzed by autoradiography on Kodak X-OMAT film after separation on a 7–15% polyacrylamide gradient denaturing gel.

The size of the proteins obtained from particular phage by hybrid selection and their cross reaction with specific antiserum is shown in Table 2.

TABLE 2

| Hybrid Phage No. | 44A | W17A | W12A |
|---|---|---|---|
| Mol. weight of major protein produced from hybrid selected message | 67,000 | 48,000 | 53,000 |
| Cross reaction of major protein with antisera against | | | |
| CBH I | + | − | − |
| CBH II | − | + | − |
| EGI | − | − | + |

This procedure permitted the construction of restriction enzyme maps of the three cellulase genes. The restriction enzyme map for EGI is shown in FIG. 1.

The nucleotide sequence of the EGI gene was generated by dideoxy sequencing (F. Sanger et al., Proc. Natl. Acad. Sci. USA 74:5463–5467 (1977)) using restriction enzyme fragments or DNA fragments obtained by the "shotgun" procedure (P. L. Deiniger, Anal. Biochem. 129:216–223 (1983)) and is shown in FIG. 2A–2C [SEQ ID No. 1]. The corresponding protein sequence that was deduced from the nucleotide sequence is also shown in FIG. 2 [SEQ ID No. 2].

EXAMPLE 2

Isolation of full length cDNAs coding for the enzymes CBH I, CBH II and EGI

A cDNA bank from T. reesei was made from induced mRNA isolated from cells as described earlier. However, after the frozen mycelia had been ground under liquid nitrogen it was suspended in 5 volumes of guanidinium isothiocyanate buffer as described by Maniatis et al. (I.

Maniatis et al. "Molecular Cloning: A Laboratory Manual," Cold Spring Harbor Laboratory, (New York 1982)). The RNA preparation was then carried out as described (J. M. Chirgwin et al., "Isolation of Biologically Active Ribonucleic Acid from Sources Enriched in Ribonuclease," Biochemistry 18:5294–5299 (1979)).

cDNA first strand synthesis was carried out according to Maniatis (T. Maniatis et al, "Molecular Cloning: A Laboratory Manual," Cold Spring Harbor Laboratory, (New York 1982)) and the second strand was carried out according to Gubler and Hoffman (Gubler and Hoffman, Gene 25:263 (1983)). The double stranded cDNA was then treated with T4-polymerase to give blunt ends and small cDNAs less than 500 nucleotides long removed by passage through a CL-4B column (Pharmacia). Long cDNAs were then ligated to a SmaI digested and phosphatase treated preparation of pUC8 vector. The ligation mixture was used to transform E. coli strain JM105 and the cDNA bank was stored on nitrocellulose filters.

Full length cDNAs coding for CBH I, CBH II and EGI were isolated from a cDNA bank using specific restriction fragments as probes. For the identification of CBH I, a radioactive EcoRI-HindIII fragment from the 5' end of the chromosomal gene was used to identify long cDNAs. A plasmid pTT01 from a clone containing sequences homologous to this EcoRI-HindIII fragment was further characterized by sequencing of the cDNA ends by double stranded dideoxy sequencing. 1 mg of purified plasmid was denatured in 0.4M NaOH at room temperature for 5 minutes at a concentration of 100 ng/μl. 5 μl of sequencing or reverse sequencing primer (Amersham) was S added and the mixture was precipitated with ethanol. After washing the pellet was resuspended in 10 μl at 14 mM Tris pH 8–7 mM MgCl$_2$. Sequencing reactions were done according to general methods (F. Sanger et al, Proc. Natl. Acad. Sci. USA 74:5463–5467 (1977)) except that temperature was kept at 37° C. CBH II cDNAs were isolated using a PvuII fragment from the 5' end of the chromosomal gene and the plasmid pTT09 characterized as for the CBH I cDNA. EGI cDNAs were identified using a KpnI-SalI fragment the 5' end of the gene and plasmid pTT11 also characterized as for the CBH I cDNA. All cDNAs were then sequenced to determine that their sequence corresponded to that of the gene from which they are transcribed.

EXAMPLE 3

The construction of expression vectors containing cDNAs for the production of fungal cellulases in yeast The efficient yeast expression vector pMA91 has been assembled using the regulatory sequences of the yeast phosphoglycerokinase (PGK) gene (J. Mellor et al, "Efficient Synthesis of Enzymatically Active Calf Chymosin in Saccharomyces Cerevisiae", Gene 24:1–14 (A. J. Kingsman & Kingsman)). The sequences coding for the amino acid sequence of the enzyme have been removed from the gene and replaced by a single BglII site. This deleted gene has then been inserted into a yeast/E. coli shuttle plasmid.

Figure 3:
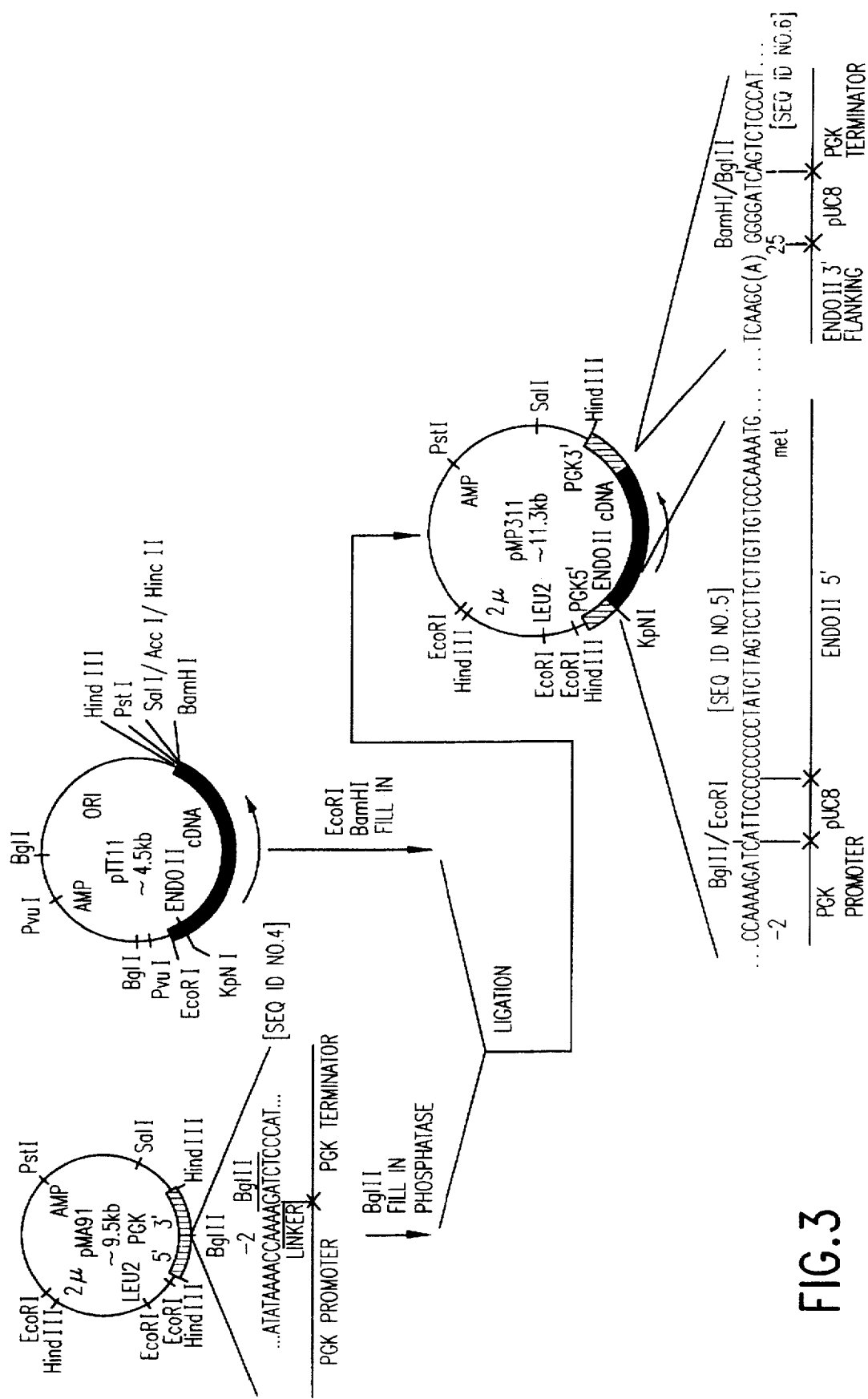
FIG. 3 shows the construction of plasmid pMP311 for expression of *T. reesei* EGI in yeast.

The EGI cDNA was transferred to pMA 91. Plasmid pMA91, the expression vector was cleaved with BglII and the ends were filled in with the Klenow fragment. The cDNA was removed from the plasmid backbone using EcoRI and BamHI. The ends of the DNA were filled in with Klenow fragment. The cDNA fragment was then isolated from an agarose gel and ligated to the vector pMA91 prepared as described herein. The pMA91vector was treated with phosphatase, ligated to the cDNA and transformed into *E. coli* strain HB101 by selection for expression of the vector amp gene (FIG. 3). Plasmid DNA was isolated from a number of transformants and those clones containing the cDNA insert in the correct orientation with respect to the PGK promotor—as identified by restriction enzyme analysis—were retained. FIG. 3 shows the DNA sequences at the junctions between pMA 91 and the EGI cDNA. The plasmid, pMP 311 containing the EGI cDNA in the correct orientation was transferred to yeast as described earlier to give strain VTT-RC-84013.

EXAMPLE 4

Culturing the hybrid yeast strains to produce the cellulolytic enzyme EGI

Strain VTT-RC-84013 (EGI cDNA) was grown in a yeast minimal medium containing arginine, histidine and adenine for three days after which complete medium ⅓ volume was added to allow the cells to pass through one more division. The final volume of the cultures was about 150 ml.

Preparation of different fractions for analysis of the location of enzyme activity Three fractions were prepared from hybrid yeast cultures for analysis of enzyme activity. Fraction 1 comprised the growth medium without the cells. Fraction 2 comprises the supernatant left when protoplasts are pelleted and fraction 3 comprises the supernatant of lysed protoplasts.

After cultivation yeast cells were collected by centrifugation and the supernatant was saved (Fraction 1). The resulting pellet was washed twice with distilled water and 1.2M sorbitol. The pellet was then resuspended in protoplasting buffer (1.2M sorbitol, 10 mM Tris and 10 mM $CaCl_2$, pH 7.6) and Zymolyase 60000 was added at a concentration of 30 µg/ml of protoplasting suspension. Suspension was incubated in a waterbath at 37° C. for 60 minutes with gentle shaking. The protoplasts so formed were pelleted and the resulting supernatant (periplasmic cell contents) (Fraction 2) saved for enzyme activity determinations. In some cases fractions 1 and 2 were concentrated by ultrafiltration (Amicon). Protoplast pellets were washed with cold 1.2M sorbitol and resuspended in 1.2 ml of 5 mM citrate buffer pH 5.0, pelleted and the supernatant was saved (Fraction 3).

EXAMPLE 5

Measurement of cellulase enzyme activity produced by the hybrid yeasts

The three different fractions were tested for endoglucanase activity by following the hydrolysis of 0.1% β-glucan at 50° C.

The reducing sugars liberated in 5 minutes (overnight) were measured as glucose using the dinitro salicylic acid method (Kirsop, B. H., *J. Inst. Brewing* 59:378 (1953)). Most of the EGI activity was found secreted into the growth medium. The EGI enzyme produced with this construction represented 1–5% of total cell protein.

EXAMPLE 6

Construction of Functional Derivatives of EGI

Materials and Methods

In addition to the materials and methods already disclosed in the examples, the following have been utilized.

Proteins and antibodies

The purified EGI protein from Trichoderma reesei VTT-D-80133 (Niku-Paavola et al., *Biochem. J.* 231:75–81 (1985)) was a kind gift from Dr. Maija-Liisa Niku-Paavola (Technical Research Centre of Finland, Espoo, Finland). Alternatively, EGI may be purified from T. reesei or from recombinant hosts expressing the full-length EGI protein using techniques known in the art (Niku-Paavola et al., *Biochem. J.* 231:75–81 (1985)). Polyclonal antiserum KH1057 against EGI was prepared at the National Public Health Institute, Helsinki, Finland, by using their standard immunization procedure. The production and characterization of the monoclonal antibody EI-2 is described in (Aho et al, *Eur. J. Biochem.* 200:643–649 (1991)).

A. Construction of the cellulolytic yeast strains

The standard recombinant DNA techniques described by Maniatis et al. (Maniatis et al., *Molecular Cloning*, Cold Spring Harbor Laboratory, New York (1982)) were used. The enzymes used in the cloning experiments were purchased from Boehringer Mannheim or New England Biolabs. *E. coli* DH5 (Hanahan, D., *J. Mol. Biol.* 166:557–580 (1983)) was used as a host for cloning the deleted cDNAs, which were prepared in vector pIBI76 (International Biotechnologies, Inc., New Haven, Conn., USA). The deleted cDNAs were prepared as described earlier (Aho and Paloheimo, *Biochim. Biophys. Acta* 1087:137–141 (1990)) and transferred to the yeast expression vector pAAH5 (Ammerer, G., *Methods in Enzymology*, Wu et al, eds., 101 C, pp. 192–201, Academic Press, New York (1983)). Plasmids containing the full length cDNAs for CBHI, CBHII, EGI and EGIII in pAAH5 (pALK220, pALK221, pALK222 and pALK223, respectively) and plasmids containing the selected, deleted cDNAs coding for truncated EGI were transformed (Ito et al., *J. Bacteriol.* 153:163–168 (1983)) into *S. cerevisiae* strain Yfl35 (MATα, leu2–3,112, his3–11,15). Yeast strains were grown in minimal medium containing 20 g glucose and 6.7 g yeast nitrogen base without amino acids (Difco) per liter and supplemented with amino acids except leucine in liquid culture, 1.5% agar was added for the solid support.

B. Endoglucanase activity assay

Recombinant yeast strains were tested for endoglucanase activity by growing the cells on the minimal agar plates as described above, supplemented with 0.5% (w/v) Ostazin brilliant red-hydroxyethyl cellulose (OBR-HEC, Sigma Chemical Co., St. Louis, Mo., USA). The hydrolysis of OBR-HEC was detected as clear zones around the growing colonies on the red background (Farkas et al., *FEMS Microbiol. Lett.* 28:137–140 (1985)).

C. Filter Immunodetection

Yeast strains were streaked onto a nitrocellulose filter (Hybond C, Amersham, UK) covering the agar plate and grown at 30° C. for 2–4 days. Filters were lifted from the plates and the cells washed off with 20 mM Tris-HCl, pH 7.5, 500 mM NaCl. The proteins on the filter were detected using the antibodies and the Protoblot Immunoblotting System (Promega, Madison, Wis., USA) according to the manufacturer's instructions.

D. Growth and fractionation of yeast cells

The liquid cultures were grown at 30° C. with shaking until the stationary phase was reached. Cells were separated by centrifugation for 15 min at 4000×g. The proteins in the culture supernatant were precipitated with 10% trichloroacetic acid for 1 h on ice. The precipitate was collected by centrifugation, neutralized with ammonium vapor and dissolved in 250 mM sodium phosphate buffer pH 7.5, containing 50 mM EDTA, 1% (w/v) n-octylglucoside and 1% (v/v) 2-mercaptoethanol. Samples were incubated at 37° C. overnight with one unit of N-glycosidase F (ONGase F, Boehringer, Mannheim Biochemica, Germany). The harvested cells were washed once, resuspended in 1/50 of the original volume of 50 mM Na-citrate buffer, pH 5.0, 1 mM phenylmethylsulphonyl-fluoride (PMSF, Sigma Chemical Co., St. Louis, Mo., USA) and broken in a French pressure cell press (Aminco, Ill., USA). The membrane fraction was separated from the soluble one by centrifugation at 10,000×g for 15 min.

E. Western Blotting

Proteins were separated on 10% polyacrylamide-SDS-gels (Laemmli, U.K., Nature 227:680–685 (1970)) and transferred electrophoretically onto nitrocellulose membrane (BA 85, Schleicher and Schuell, Dassel, Germany) using the small scale electrophoresis and transfer system (Bio-Rad, Richmond, Calif., USA). The membranes were immunostained with the monoclonal antibody EI-2, and developed using the Protoblot Immunoblotting System (Promega, Madison, Wis., USA).

Figure 4A:
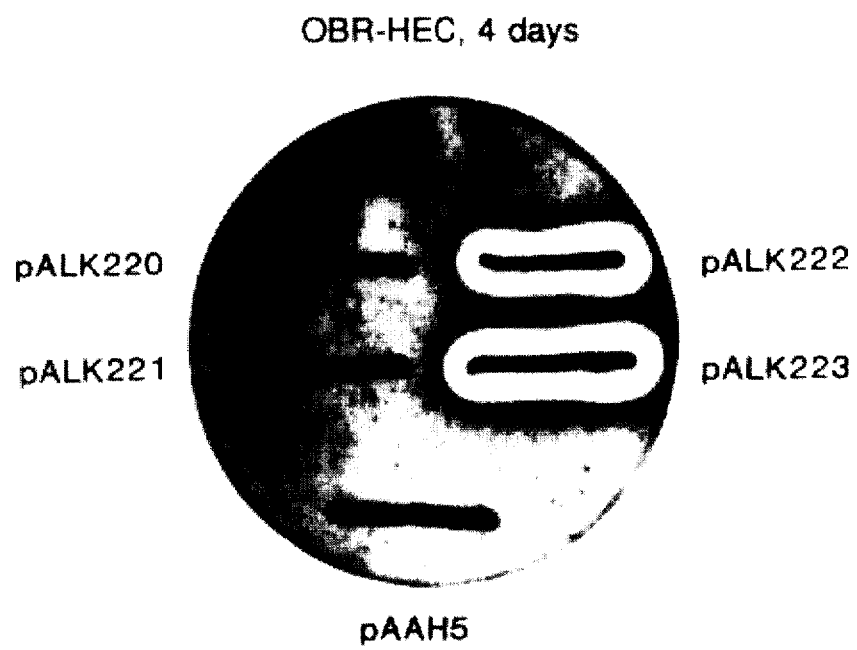
FIGS. 4A–4B shows cellulolytic yeast strains expressing CBHI, CBHII, EGI and EGIII enzymes under the control of the yeast ADH1 promoter. The yeast were grown for 4 days on a nutrient plate containing 0.5% OBR-HEC (FIG. 4A) or on the nitrocellulose filter covered plate (FIG. 4B). Hydrolysis of the substrate was documented by photographing the plate (FIG. 4A). The filter was immunologically stained using KH1057 antiserum (1/5000) (FIG. 4B).
Figure 4B:
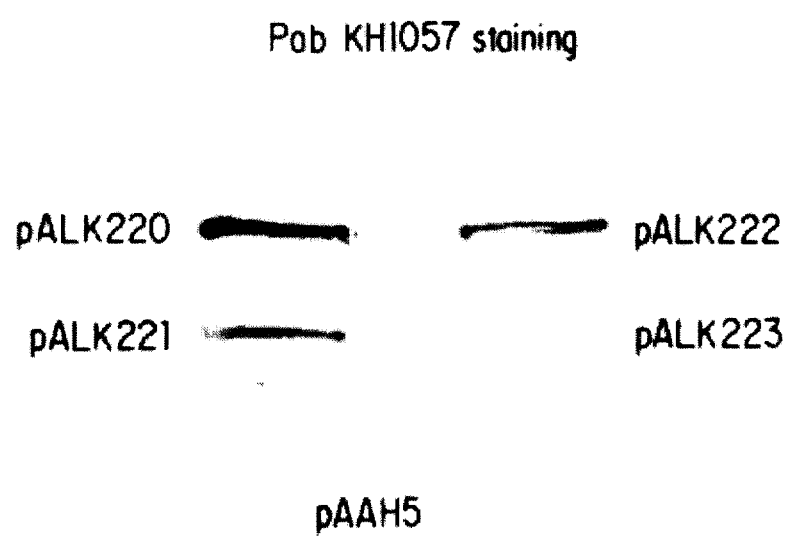

F. The expression of cellulase cDNAs in yeast cDNAs for four T. reesei cellulases were expressed in S. cerevisiae. Their own signal sequences were used to conduct the secretion of the enzyme. The endoglucanase producing colonies formed a clear halo on the pink background. The yeast endogenous glucanases did not degrade the substrate used (FIG. 4A). Cellobiohydrolases secreted from yeast were not able to degrade HEC, but they were demonstrated by immunostaining with the cross-reacting polyclonal antiserum against EGI, KH1057 (FIG. 4B).

G. The secretion of truncated proteins

Figure 5:
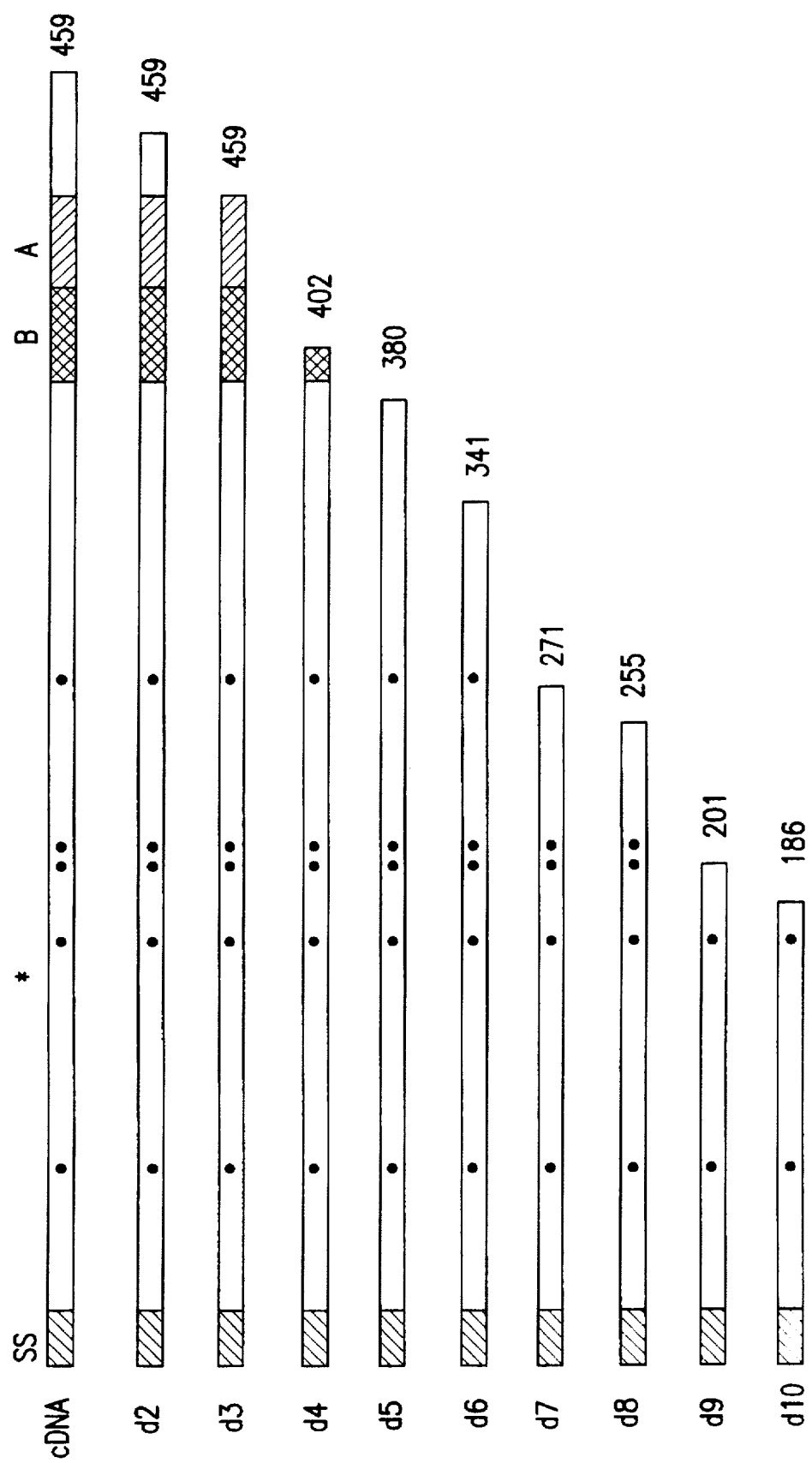
FIG. 5 shows a series of 3'-end deletions of EGI cDNA. The number of EGI amino acids in each protein encoded by the deleted cDNA is shown. The potential N-glycosylation sites are shown by heavy dots. The location of the active site is shown by an asterisk. The signal sequence (SS), the Thr-Ser-rich region (B), and the conserved region (A) are shown. The open box to the left of the BA domain represents the core domain and the open box to the right denotes the 3'-untranslated region of EGI cDNA.
Figure 6A:
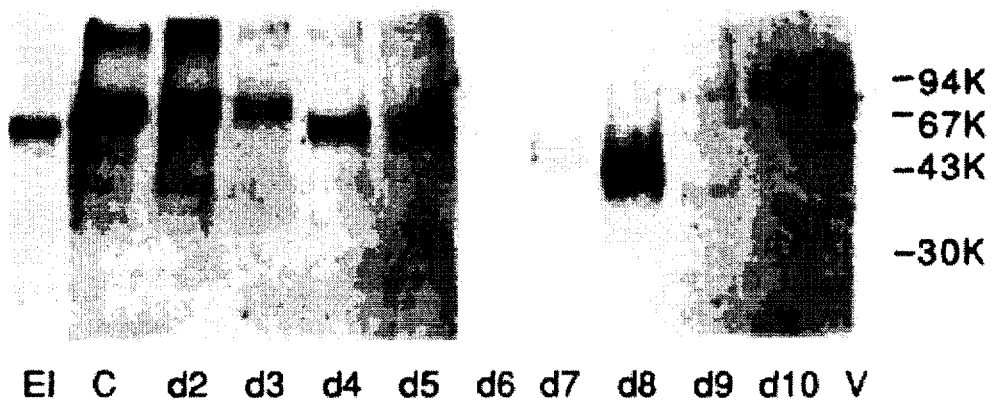
FIG. 6A–6C.
Figure 6B:
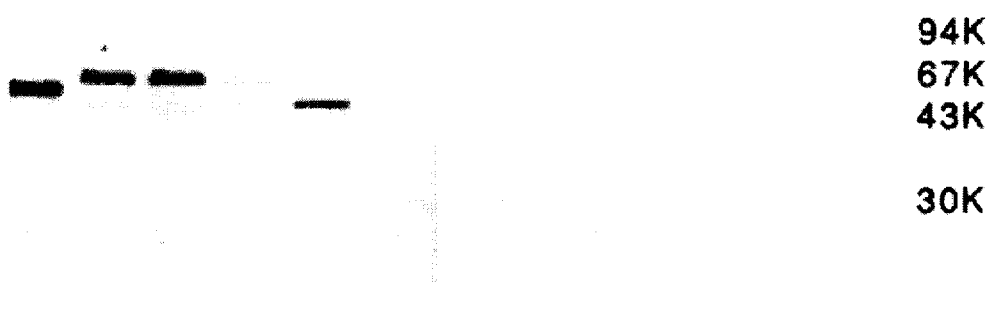
Figure 6C:

The truncated proteins were expressed from the deleted cDNAs (FIG. 5). The deletion d2 lacked half of the 3'-end untranslated region but contained the intact EGI translation stop codon. The deletion d3 coded the full length protein, but lacked the translation stop codon and thus was expressed as a fusion protein containing the last 44 COOH-terminal amino acids of ADC1. Also d4 and d9 formed similar type of fusion proteins. Deletions d6, d7 and d10 were expressed as fusion proteins bearing 38 extra amino acids coded by the COOH-terminal region of the ADC1 gene but not in the ADC1 reading frame. Deletions d5 and d8 had only two extra amino acids before reaching the translation stop codon in the ADC1 cassette. The proteins encoded by the full length cDNA and all the deletions except d10, were found in the particulate fraction of yeast cells (FIG. 6C). The soluble fraction contained proteins encoded by the full length cDNA and deletions d2, d3 and d4 (FIG. 6B). In addition to the protein encoded by the intact cDNA, the proteins encoded by deletions d2, d4 and d8 were found in the yeast culture medium (FIG. 6A). A weak band of proteins encoded by d3, d5, d7 and d9 could also be detected in the medium, but nothing was detected from d6 and d10.

H. The enzymatic activity of the truncated EGI proteins

Figure 7A:
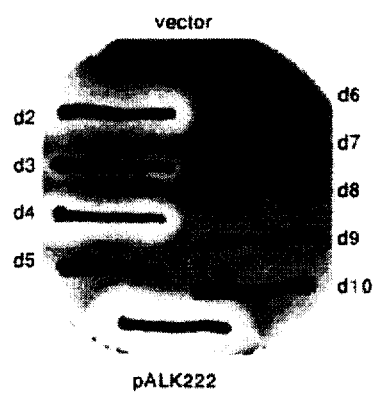
FIGS. 7A–7C shows EGI produced from the deleted cDNAs. The EGI was expressed under the control of the yeast ADH1 promoter. Yeast strains containing the full length EGI cDNA, pALK222, the expression vector pAAH5, and the deleted EGI cDNAs d2–d10 were grown on the plates containing 0.5% OBH-HEC at 30° C. for 2 days (FIG. 7A) and for 6 days (FIG. 7B), at which time the size of the clearing was documented by photography. The proteins secreted from the yeast strains grown on the nitrocellulose filter covered plate were immunodetected using the Mab EI-2, diluted 1:2500.
Figure 7B:
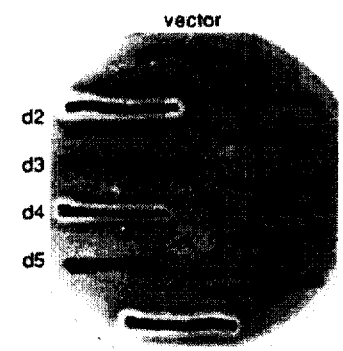
Figure 7C:
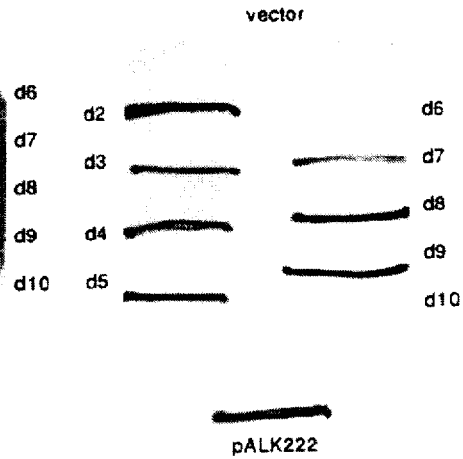

The yeast strains containing the deleted EGI cDNAs were grown on the nutrient agar plate containing OBR-HEC as the substrate and indicator for the EGI enzyme activity (FIG. 7A, B). Deletion 4, which produced a polypeptide with the entire core region plus eight amino acids from the B-region, still made active enzyme, but deletion 5, producing a polypeptide missing 13 COOH-terminal amino acids from the core region did not produce active enzyme. The small hydrolysis halo around the d3 containing yeast strain was due to the inefficient secretion of the EGI enzyme (FIG. 6A). The type of the COOH-terminal fusion did not correlate with the efficiency of secretion of the truncated proteins. The secretion of the truncated proteins from the yeast cells was confirmed by immunostaining the nitrocellulose filter on which the yeast strains had grown for four days (FIG. 7C). The Mab EI-2 gave clear staining with all strains except d6 and d10. This is consistent with the Western blot (FIG. 6), which showed that d6 coded for an immunodetectable protein, which was not secreted. The protein encoded by d10 probably did not contain any antigenic epitope for Mab EI-2.

EXAMPLE 7

In vitro mutagenesis of EGI

Unless otherwise described, materials and methods are as presented in Nitisinprasert, S. Dissertation, Univ. Helsinki, Helsini, Finland, 1990, and Mitsuishi, Y. et al. FEBS Lett. 275:135–138 (1991), both incorporated herein by reference.

Figure 8:
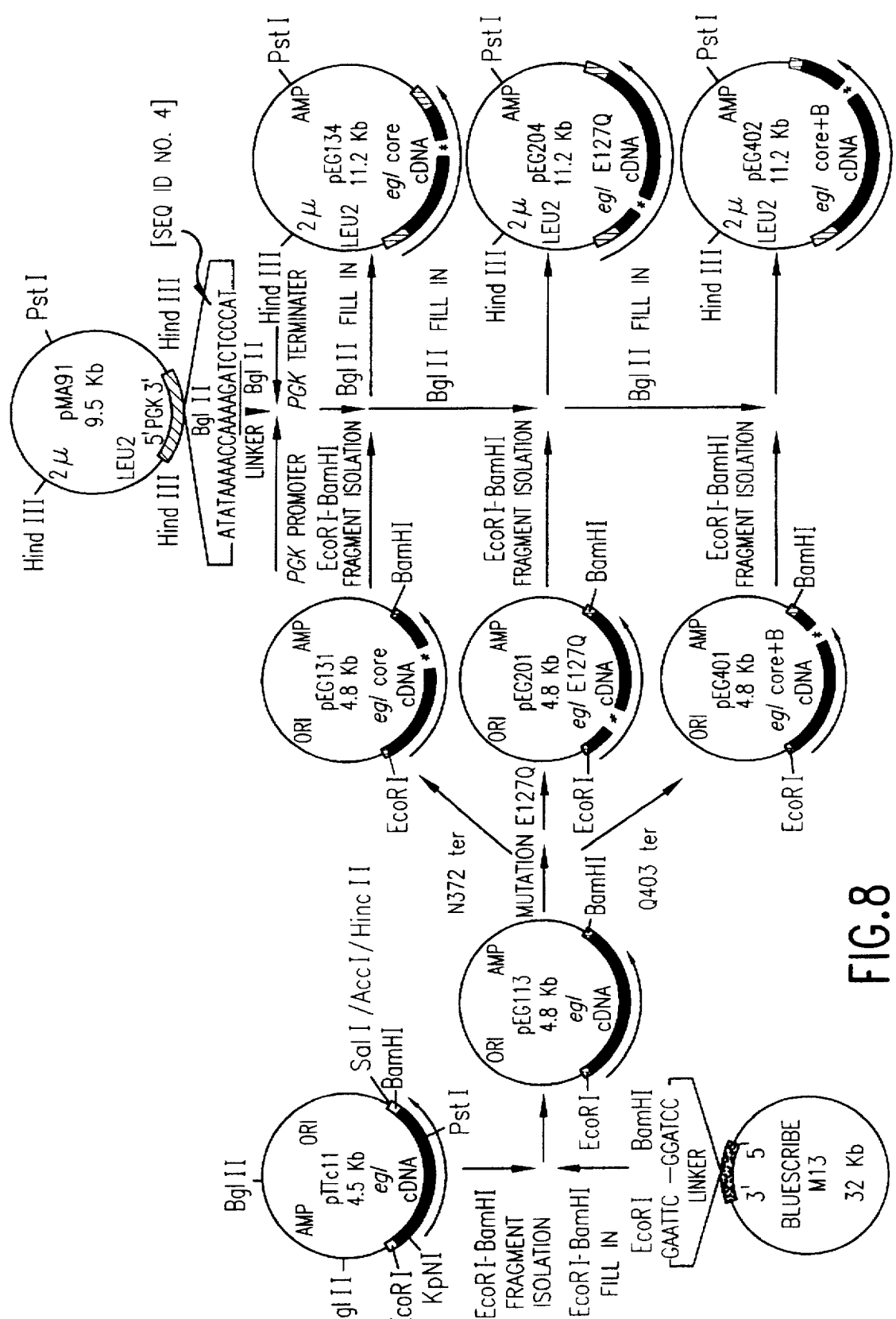
FIG. 8 discloses the construction of vectors for the expression of egl1 and its mutant forms in yeast. The cDNAs are shown as a black block. (*) represents a mutation site. These constructions utilize the yeast PGK promoter for expression of EGI.

Full-length egl1 cDNA was cloned into the linker site of a Bluescribe M13+ vector as shown in FIG. 8 and the expression plasmids were transformed into E. coli. The host strain JM101 was used in order to obtain high yields of single stranded DNA. (Paper V, Nitisinprasert, S. Dissertation, Univ. Helsinki, Helsini, Finland, 1990, incorporated herein by reference).

Oligonucleotides E1 (Asn (394)), E2 (Gln (425)) and E3 were used as shown in Table IV. Each created new restriction sites (Table IV) which were useful in screening by restriction mapping. The mutagenesis was performed by the method of Sayer et al., Nucl. Acids Res. 16:791–802 (1988) with some modifications to improve yield. Specifically, at the exonuclease digestion step, 500 mM NaCl was omitted as it was found that NaCl inhibited the exonuclease activity. In this way, the mutant yields obtained were between 10 and 75%. The highest yields were obtained when a nitrocellulose filtration step was used to remove contaminating single-stranded temples. Asparagine 394 and glutamine 425 were changed to the stop codon TAG.

TABLE IV

Plasmids, mutations and recombinant yeast strains

| Protein | Purpose | Plasmid | Mutation and the oligo-nucleotide used | Change on site | Recombinant yeast strain |
|---|---|---|---|---|---|
| EGI | Wild type | **pM311 | — | — | H310 |
|  | core protein | pEG134 | N394ter***(E1) | SnaBI, MaeII and SalI created | H312 |
|  | active site | pEG204 | E149Q(E3) | TthII and PvuII created | H313 |
|  | core + B protein | pEG402 | Q425ter*(E2) | AccI created | H311 |
|  | Vector | pMA91 | — | — | H314 |

*Penttilä et al., Gene 63:103–112(1988), Penttilä et al., Yeast 3:175–185(1987), *ter, stop codon The mutated cDNAs of egl1 were inserted into pMA91 as shown in FIG. 8 and transformed into a laboratory yeast strain. The strain AH22 was chosen due to its good growth. The resulting recombinant yeast strains obtained are listed in Table IV.

All the yeast strains containing chimeric plasmids with mutated genes grew in the same manner as the corresponding strains carrying wild type genes. The enzymes were secreted into the growth media at the stationary phase.

The overglycosylation of EGI expressed in the yeast host resulted in extensive heterogeneity of the proteins, which may hamper their purification. Therefore, an immunological method using specific monoclonal antibody is most useful for quantification of the proteins. The mutated EGI is secreted in somewhat lower amounts than the wild type EGI.

Figure 9:
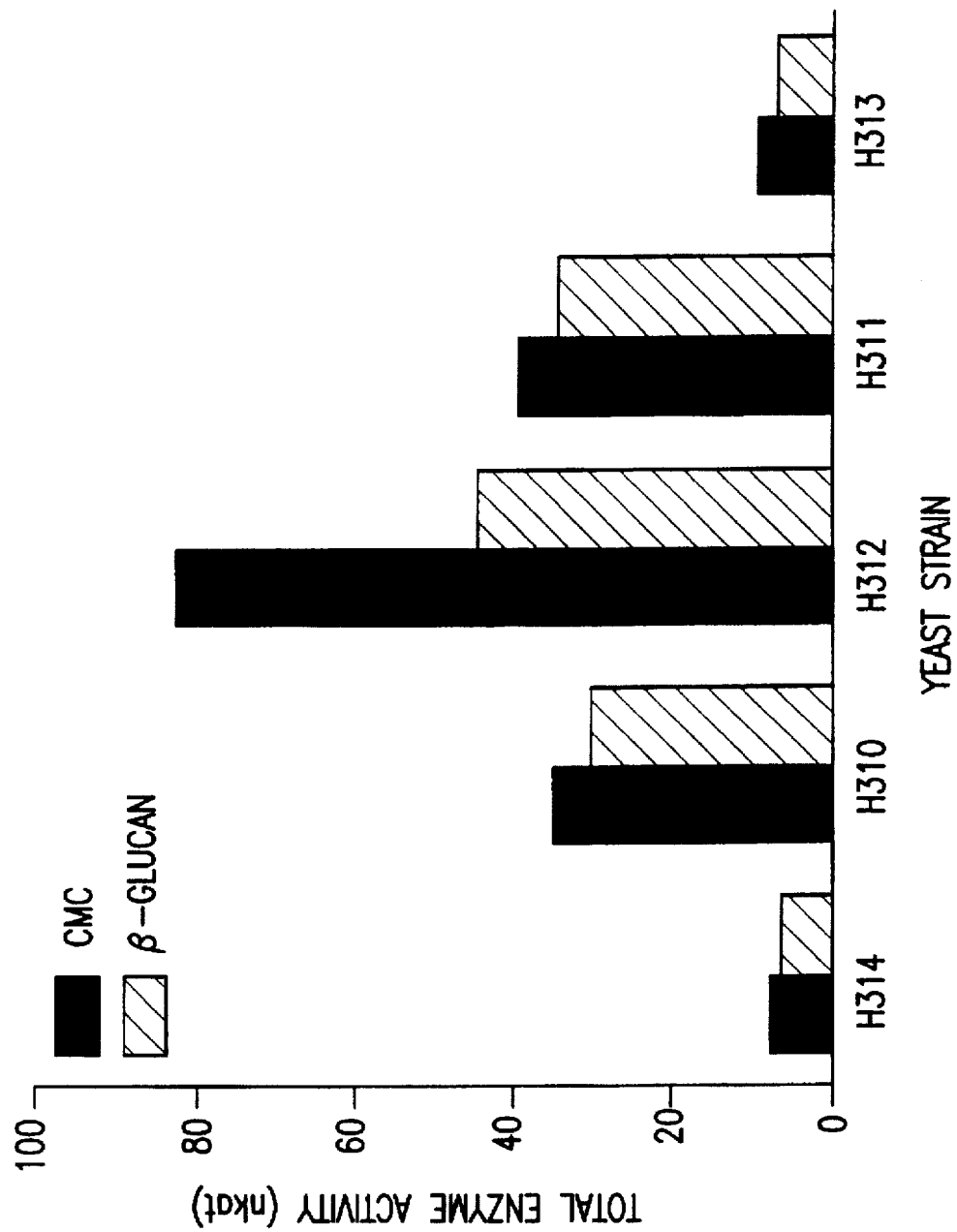
FIG. 9 shows a comparison of total secreted enzyme activity of EGI and its mutants against CMC and β-glucan. Yeast strain H314 contained pMA91, H310 contained EGI wild type, H312 contained EGI core, H311 contained EGI core+B, and H313 contained EGI E127Q (Mitsubishi et al., *FEBS Lett.* 275:135–138 (1990)). All strains were grown at the same growth rate in 50 ml of SC-leu medium. These constructions until the yeast PGK promoter for expression of EGI.

The recombinant yeast strains H314 containing pMA91, H310 producing wild type EGI (EGI wt), H312 producing EGI core and H311 producing EGI core+B were grown in SC-leu medium and the secreted proteins were studied. The wild type EGI is active towards 1,4-glycosidic bonds in β-glucan and in substituted cellulose (CMC). All of the new recombinant strains produced enzymes which could hydrolyze these two substrates with different efficiencies (FIG. 9). The recombinant yeast strain H312 producing EGI core protein showed higher total activity against both substrates that the strain H310 producing EGI wild type, whereas the activity of the strain H311 producing EGI core+B protein was equal to that of the wild type strain.

A comparison of the activities against CMC and β-glucan revealed the interesting result that the core protein produced by strain H312 had higher activity against the substituted substrate CMC than against β-glucan.

All references referred to are incorporated herein by reference. It is considered that the invention and many of its attendant advantages will be understood from the foregoing description and that it will be apparent that various changes may be made in the steps of the described method for mature protein synthesis without departing from the spirit and scope of the invention or sacrificing all of its material advantages, the method hereinbefore described being merely a preferred embodiment.

What is claimed is:

1. A recombinant molecule which comprises a nucleic acid sequence of the KpnI-SalI fragment that is between base 86 and base 304 of FIG. 2 or a single or multiple base substitution of said sequence that encodes the amino acid sequence of said fragment as shown in FIG. 2.

2. The recombinant DNA molecule of claim 1 wherein said nucleic acid sequence has the DNA sequence of the KpnI-SalI sequence shown on FIG. 2.

3. A cloning vector comprising the recombinant DNA molecule of claim 1 or 2.

4. The cloning vector of claim 3, wherein said coding sequence of said shorter EGI protein is operably linked to transcriptional expression elements.

5. A host cell transformed with the recombinant DNA molecule of claim 1 or 2.

6. The host cell of claim 5, wherein said DNA molecule further comprises a cloning vector.

7. A method of producing fragments of EGI, which method comprises:

A. providing tee DNA molecule encoding the shortened EGI protein of any one of claims 1 or 2;

B. transforming a host with said DNA molecule; and

C. expressing said shortened EGI protein.

\* \* \* \* \*

UNITED STATES PATENT AND TRADEMARK OFFICE
CERTIFICATE OF CORRECTION

PATENT NO. : 5,766,915
DATED : June 16, 1998
INVENTOR(S) : Knowles, et al

It is certified that error appears in the above-identified patent and that said Letters Patent is hereby corrected as shown below:

Claim 1, column 33, line 56, after "recombinant", please insert --DNA--.

Claim 4, column 33, line 65, please delete "coding".

Claim 4, column 33, line 66, please delete "of said shorter EGI protein" and insert --that encodes said amino acid sequence--.

Claim 7, column 34, line 62, please delete "tee" and insert therein

--said recombinant--.

Column 34, line 62 at claim 7, after "molecule" please delete "encoding the shortened EGI protein".

Column 34, line 65, at claim 7, please delete "protein" and insert therein --fragments--.

Signed and Sealed this

Twenty-third Day of March, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,766,915
DATED : June 16, 1998
INVENTOR(S) : Knowles et al.

It is certified that error appears in the above-identified patent and that said Letters Patent is hereby corrected as shown below:

<u>Title page,</u>
Item [*] Notice, "U.S. Patent No. 5,343,670" should be deleted and replaced with -- U.S. Patent No. 5,393,670 --.

Signed and Sealed this

Fifteenth Day of November, 2005

JON W. DUDAS
*Director of the United States Patent and Trademark Office*